US007148193B2

(12) United States Patent
Blume et al.

(10) Patent No.: US 7,148,193 B2

(45) **Date of Patent: *Dec. 12, 2006**

(54) COMPOUNDS THAT BIND TO GROWTH HORMONE RECEPTOR

(75) Inventors: Arthur J. Blume, Annandale, NJ (US); Renee Brissette, Clarksburg, NJ (US); Juan Carcamo, New York, NY (US); Wlodek S. Mandecki, Princeton Junction, NJ (US); Pauline M. Tang, Pearland, TX (US)

(73) Assignee: Antyra, Inc., Edison, NJ (US)

(*) Notice: Subject to any disclaimer, the term of this patent is extended or adjusted under 35 U.S.C. 154(b) by 535 days.

This patent is subject to a terminal disclaimer.

(21) Appl. No.: 10/117,553

(22) Filed: Apr. 4, 2002

(65) Prior Publication Data

US 2006/0252697 A1 Nov. 9, 2006

Related U.S. Application Data

(63) Continuation-in-part of application No. 08/990,888, filed on Dec. 15, 1997, now Pat. No. 6,387,879.

(51) Int. Cl.
*A61K 38/04* (2006.01)

(52) U.S. Cl. .................. 514/13; 424/193.1; 424/198.1; 530/300; 530/326; 530/399

(58) Field of Classification Search ................... 514/13
See application file for complete search history.

(56) References Cited

U.S. PATENT DOCUMENTS 6,387,879 B1 * 5/2002 Blume et al. ................. 514/13

OTHER PUBLICATIONS degli Unerti EC, Trasforini G, Salvadori S, Margutti A, Tomatis R, Rotola C, Bianconi M, Pansini R. "Stimulatory effect of dermorphin, a new synthetic potent opiate-like peptide, on human growth hormone secretion" *Neuroendocrinology*, Oct. 1983, 37(4):280-3.

Luvnah O, Stura EA, Johnson DL, Middleton SA, Mulcahy LS, Wrighton NC, Dower WJ, Jolliffe LK, Wilson IA. "Functional mimicry of a protein hormone by a peptide agonist: the WPO receptor complex at 2.8 A." *Science*. Jul. 26, 1996, 273(5274):464-71.

Eason MG, Francis RS, Kuhn CM. "mu-Opioid agonists stimulate growth hormone secretion in immature rats" *Neuroendocrinology*, Jun. 1996, 63(6):489-97.

Muruais J, Penalva A, Dieguez C, Casanueva FF. "Infuence of endogenous cholinergic tone and alpha-adreneric pathways on growth hormone responses to His-D-Trp-Ala-Trp-D-Phe-Lys-NH2 in the dog" *J Endocrinol*. Aug. 1993, 138(2):211-8.

Wells JA. "Hormone mimicry" *Science*, Jul. 26, 1996, 273(5274):449-50.

(Continued)

*Primary Examiner*—Robert A. Wax
*Assistant Examiner*—Marsha Tsay
(74) *Attorney, Agent, or Firm*—Morgan & Finnegan, L.L.P.

(57) ABSTRACT

The present invention provides peptides that bind to the active site of the growth hormone receptor. The present invention also provides methods of using these peptides to identify small organic molecules, which are novel agonists or antagonists of the growth hormone receptor. In addition, the present invention provides kits and therapeutic compositions comprising the peptides that bind to growth hormone receptor.

6 Claims, 20 Drawing Sheets

OTHER PUBLICATIONS

Moore GJ. "Discovery and design of peptide mimetics" *Proc West Pharmacol Soc.* 1997;40:115-9.

Wrighton NC, Farrell FX, Chang R, Kashyap AK, Barbone FP, Mulcahy LS, Johnson DL, Barrett RW, Jolliffe LK, Dower WJ. "Small peptides as a potent mimetics of the protein hormone erythropoietin" *Science.* Jul. 26, 1996, 273(5274):458-64.

Braisted A. "Hormone peptidomimetics:seeing double" *Nat Biotechnol.* Nov. 1997, 15(12):1244-5.

Hruby VJ, Ahn JM, Liao S. "Synthesis of oligopeptide and peptidomimetic libraries" *Curr Opin Chem Biol.* Jun. 1997;1(1):114-9.

Kieber-Emmons T, Murali R, Greene MI, "Therapeutic peptides and peptidomimetics" *Curr Opin Biotechnol.* Aug. 1997; 8(4):435-41.

Yanofsky SD, Baldwin DN, Butler JH, Holden FR, Jacobs JW, Balasubramanian P, Chino Jp, Cwirla SE, Peters-Bhatt E, Whitehorn EA, Tate EH, Akeson A, Bowlin TL, Dower WJ, Barrett RW. "High affinity type I interleukin 1 receptor antagonists discovered by screening recombinant peptide libaries" *Proc Natl Acad Sci U S A.* Jul. 9, 1996, 93(14):7381-6.

Cwirls SE, Balasubramanian P, Duffin DJ, Wagstrom CR, Gates CM, Singer SC, Davis AM, Tansik RL, Mattheakis LS, Boytos CM, Schatz PJ, Baccanari DP, Wrighton NC, Barrett RW, Dower WJ, "Pepetide agonist of the thrombopoietin receptor as potent as the natural cytokine" *Science.*Jun. 13, 1997, 276(5319):1696-9.

Katz BA. "Structural and mechanistic derterminants of affinity and specificity of ligands discovered or engineered by phage display" *Annu Rev Biophys Biomol Struct.* 1997; 26:27-45.

F. Martin, C. Toniatti, A.L. Salvati, S. Venturini, G. Ciliberto, R. Cortese, M. Sollazo, 1994, "The affinity-selection of minibody polypeptide inhibitor of human interleukin-6" *EMBO J.* 13:5303-5309.

B.S. Wang, A.L. Lumanglas, C.A. Bona, T.M. Morna, 1996, "Functional characterization of monoclonal antibodies specific to growth hormone receptor" *Mol. immunol.* 33:1197-1202.

C.D. Partidos, C.L. Chirinos-Rojas, M.W. Steward, 1997, "The potential of comibnatorial peptide libraries for the indetification of inhibitors of THF-α mediated cytotxicity in vitro" *Immunol. Lett.* 57:113-116.

S.C. Souza, G.P. Frick, X. Wang, J.J. kopchick, R.B. Lobo, H.M. Goodman, 1995, "A single arginine residue determines species specificity of the human growth hormone" *Proc. Natl. Acad, Sci. USA* 92:959-963.

Z. Guo, D. Zhou, P.G. Schultz, 2000, "Designing small-molecule switches for protein-protein interactions" *Science* 288:2042-2045.

U.S. Appl. No. 08/990,888, filed Dec. 15, 1997, Blume et al.,

* cited by examiner

Binders

| | | | | | | | | | | | | | | | | | | |
|---|---|---|---|---|---|---|---|---|---|---|---|---|---|---|---|---|---|---|
| L | C | Q | S | L | G | V | T | Y | P | G | W | L | A | G | W | C | A | (SEQ ID NO:16) |
| M | | | $^{28}$R | $^{2}$W | $^{2}$Q | $^{6}$I | $^{22}$G | $^{47}$W | | | | V | $^{7}$T | A | | | $^{2}$G | |
| | | | $^{2}$T | F | A | $^{5}$A | $^{8}$S | $^{3}$F | | | | I | $^{3}$V | | | | $^{2}$S | |
| | | | $^{2}$N | | E | $^{d}$D | $^{5}$R | | | | | | $^{2}$S | | | | R | |
| | | | A | | P | $^{3}$L | $^{4}$K | | | | | | $^{2}$W | | | | | |
| | | | | | V | $^{2}$P | $^{2}$A | | | | | | D | | | | | |
| | | | | | R | E | $^{2}$N | | | | | | | | | | | |
| | | | | | | F | W | | | | | | | | | | | |
| | | | | | | | L | | | | | | | | | | | |

Consensus

| | | | | | | | | | | | | | | | | | | |
|---|---|---|---|---|---|---|---|---|---|---|---|---|---|---|---|---|---|---|
| L | **C** | **Q** | R | L | G | I | G | W | **P** | **G** | **W** | L | A | G | **W** | **C** | A | (SEQ ID NO:63) |
| | | | T | | | A | S | | | | | | T | | | | | |
| | | | | | | D | R | | | | | | V | | | | | |
| | | | | | | L | K | | | | | | | | | | | |

Pepitdes

| | | | |
|---|---|---|---|
| ● | control | DYKDWCLTLQPLVWASGGGYCA | (SEQ ID NO:10) |
| ○ | H5 WT | DYKDLCQSLGVTYPGWLAGWCA | (SEQ ID NO:8) |
| ■ | H5-447 | DYKDLCQRLGVGWPGWLSGWCA | (SEQ ID NO:11) |
| □ | H5-418 | DYKDLCQSWQVTWPGWLAGWCA | (SEQ ID NO:12) |
| ⊖ | H5-445 | DYKDLCQRLGVGWPGWLAGWCA | (SEQ ID NO:13) |
| o | H5-443 | DYKDLCQRLGVTWPGWLAGWCA | (SEQ ID NO:14) |

Biotin-Peptide 447 (SEQ ID NO:11)

Biotin-Peptide 447 (SEQ ID NO:11)

- □ bovine GH
- ○ control peptide
- ● H5 WT (SEQ ID NO:8)
- ■ H5-447 (SEQ ID NO:11)

- ○ control peptide
- ● H5 WT (SEQ ID NO:8)
- ■ H5-447 (SEQ ID NO:11)

| PEPTIDES | SEQ ID NO | ROUND 1 | ROUND 2 | ROUND 3 | ROUND 4 |
|---|---|---|---|---|---|
| LCQSLGVTYPGWLAGWCA | 16 | 9 | 16 | 7 | 1 |
| LCQSLG**I**TYPGWLAGWCA | 17 | 2 | 2 | | |
| LCQ**T**LGVTYPGWLAGWCA | 18 | 1 | | | |
| LCQSLGV**K**YPGWLAGWCA | 19 | 1 | | | |
| LCQSLGV**K**YPGWL**T**GWCA | 20 | 1 | | | |
| LCQSLGVTYPGWL**S**GWCA | 21 | 1 | | | |
| LCQSLGV**A**YPGWLAGWCA | 22 | 1 | | | |
| LCQSLGVT**F**PGWL**S**GWCA | 23 | 1 | | | |
| LCQ**A**LGVTYPGWLAGWCA | 24 | 1 | 1 | | |
| LCQSLGV**S**YPGWLAGWCA | 25 | 2 | | | |
| LCQSLGVTYPGWLA**A**WC**R** | 26 | 1 | | | |
| LCQSLGVTYPGWL**D**GWCA | 27 | | 1 | | |
| LCQSLGV**S**YPGWL**V**GWCA | 28 | | 1 | | |
| LCQ**T**LGV**K**YPGWLAGWCA | 29 | | 1 | | |
| LCQSLG**L**TYPGWLAGWC**G** | 30 | | 1 | | |
| LCQSLG**EA**YPGWLAGWCA | 31 | | 1 | | |
| LCQ**R**LG**L**T**W**PGWLAGWCA | 32 | | 1 | | |
| LCQSLGV**WW**PGWLAGWCA | 33 | | 1 | | |
| LCQSLG**F**TYPGWLAGWCA | 34 | | 1 | | |
| LCQSLGVTYPGWLAGWC**S** | 35 | | 1 | | |
| LCQSLGVTYPGWL**V**GWCA | 36 | | 1 | | |
| LCQSL**A**VTYPGWLAGWCA | 37 | | 1 | | |
| LCQSLGV**R**YPGWLAGWCA | 38 | | 2 | | |
| LCQSLGV**L**YPGWLAGWCA | 39 | | 1 | | |
| LCQSLG**P**TYPGWLAGWCA | 40 | | 2 | | |
| **M**CQSLGVTYPGWLAGWCA | 41 | | 1 | | |
| LCQSLG**LR**YPGWLAGWCA | 42 | | 1 | | |
| LCQSLGVTYPGWLAGWC**G** | 43 | | 1 | | |

Fig. 15a

| | | | |
|---|---|---|---|
| LCQ**R**LGVT**W**PGWLAGWCA | 44 | 2 | 2 |
| LCQSLG**A**T**W**PGWLAGWCA | 45 | 1 | |
| LCQ**R**LGV**SW**PGWLAGWCA | 46 | 2 | 1 |
| LCQSL**P**V**R**YPGWL**S**GWC**S** | 47 | 1 | |
| LCQ**R**LGV**GW**PGWLAGWCA | 48 | 3 | 5 |
| LCQ**N**LG**I**T**W**PGWLAGWCA | 49 | 1 | |
| LCQSLGVT**F**PGWLAGWCA | 50 | 1 | |
| LCQSLG**DK**YPGWLAGWCA | 51 | 1 | 3 |
| LCQSLGV**GW**PGWLAGWCA | 52 | 1 | 3 |
| LCQ**R**LGVT**W**PGWL**T**GWCA | 53 | 1 | |
| LCQSLGVTYPGWL**T**GWCA | 54 | 1 | |
| LCQSLG**A**TYPGWL**W**GWCA | 55 | 1 | |
| LCQSLG**D**TYPGWLAGWCA | 56 | 1 | |
| LCQSLGV**G**YPGWLAGWCA | 57 | 1 | 2 |
| LCQSLGVT**W**PGWLAGWCA | 58 | 3 | 4 |

Fig. 15b

| | | |
|---|---|---|
| LCQ**R**LGVTYPGWLAGWCA | 59 | 1 |
| LCQ**R**LG**A**T**W**PGWLAGWCA | 60 | 2 |
| LCQSLGV**NW**PGWLAGWCA | 61 | 1 |
| LCQSLGV**SW**PGWL**T**GWCA | 62 | 1 |
| LCQ**R**LG**IGW**PGWLAGWCA | 63 | 1 |
| LCQ**R**LGV**GW**PGW**V**AGWCA | 64 | 1 |
| LCQSLGV**S**YPGWL**T**GWCA | 65 | 1 |
| LCQ**H**LGVT**W**PGWLAGWCA | 66 | 1 |
| LCQSLG**IG**YPGWL**T**GWCA | 67 | 1 |
| LCQ**R**L**V**V**GW**PGWLAGWCA | 68 | 1 |
| LCQ**R**LGVT**W**PGW**I**AGWCA | 69 | 1 |
| LCQS**WQ**VT**W**PGWLAGWCA | 70 | 2 |
| LCQ**R**L**EA**T**W**PGWL**V**GWCA | 71 | 1 |
| LCQSLGV**GW**PGWL**T**GWCA | 72 | 1 |
| LCQSLGV**N**YPGWLAGWCA | 73 | 1 |
| LCQ**RF**GV**GF**PGWLAGWCA | 74 | 1 |
| LCQ**N**LGVT**W**PGWLAGWCA | 75 | 1 |
| LCQ**R**LGV**GW**PGWL**S**GWCA | 76 | 1 |
| LCQ**R**LGVT**W**PGWL**W**GWCA | 77 | 1 |
| LCQSL**RVRQ**PGWL**S**GWCA | 78 | 1 |

Fig. 15c

COMPOUNDS THAT BIND TO GROWTH HORMONE RECEPTOR

RELATED APPLICATION

This is a continuation-in-part of U.S. application Ser. No. 08/990,888, filed Dec. 15, 1997, now U.S. Pat. No. 6,387,879, issued May 14, 2002, which is incorporated herein in its entirety.

BACKGROUND AND SUMMARY OF THE INVENTION

Growth hormone (GH), also referred to as somatotropin, plays an important role in animal growth and development. It regulates a variety of physiological effects, including linear growth of the animal, lactation, differentiation, and electrolyte balance. The molecular mechanism of these biological effects involves the binding of growth hormone to a specific plasma membrane receptor, referred to as growth hormone receptor (GHR).

Growth hormones from different species share a significant level of sequence homology. Human GH (huGH) is a polypeptide chain of 190 amino acids and a molecular weight of 22 kDa, while rat GH is 189 amino acids long and has 64% sequence homology to its human counterpart. Growth hormone binds to a GHR, which consists of three domains: an extracellular hormone-binding domain, which is 28 kDa for the human GHR, a single pass transmembrane domain and an intracellular domain, which is 35 kDa for the human GHR.

A soluble form of the extracellular domain occurs naturally in blood as a growth hormone binding protein (GHBP). The molecular interactions between GH and membrane-bound GHR are thought to be analogous to those between GH and soluble GHBP. Receptor activation requires simultaneous binding of two GHR by one GH, i.e., receptor dimerization, to form a complex wherein the two intracellular domains can initiate the process of signal transduction underlying GH activity. Rat GHBP (rGHBP), like its membrane-bound form (rGHR), is fully cross-reactive with both human and rat GH (rGH). The human GHR, and human GHBP, can bind only the human GH (huGH) and not the rGH.

The ability to control the activation of GHR is important in developing new therapies for certain diseases such as dwarfism and acromegaly. Recombinant huGH is presently on the market as a drug for dwarfism. Injectable formulations of bovine GH also are used in animal husbandry to promote growth and milk production in cows.

Although proteins have become highly visible as potential drugs, their use as therapeutics presents several difficult problems, including the high cost of production and formulation, administration via injection, and limited stability in the bloodstream. Therefore, much effort has been made in replacing proteins, including GH, with small molecular weight molecules or peptides.

As an example, Yanofsky et al. (*PNAS* 93:7391–7386) describe the isolation of a monomer peptide antagonistic to IL-1 with nanomolar affinity for the IL-1 receptor. This effort required construction and use of many phage-display peptide libraries and sophisticated phage panning procedures.

Wrighton et al. (*Science,* 278:458–463) and Livnah et al. (*Science,* 273: 469–471) report dimer peptides that bind to the erythropoietin (EPO) receptor with full agonistic activity in vivo. These peptides are cyclical and have intra-peptide disulfide bonds. Like the IL-1 receptor antagonist, they show no significant sequence identity to the natural ligand. Importantly, X-ray crystallography revealed that the spontaneous formation of non-covalent homodimers enabled the peptides to dimerize EPO receptors.

Most recently, Cwirla et al. (*Science,* 276:1696–1699) describe the identification of two families of peptides that bind to the human thrombopoietin (TPO) receptor and are competed by the binding of the natural ligand TPO. The peptides with highest affinity, when dimerized by chemical means, proved to be in vivo agonists as potent as TPO.

Until now, no efforts have produced a successful GH-replacement drug. A key problem to replacing GH, as with some other proteins, is that a small molecule that binds to one receptor site would act as an antagonist. A dimer of two small molecules, capable of binding to two receptor units and dimerizing them, is required for agonist activity. Before this invention, there was no assay for identifying such dimers.

The present invention encompasses peptides that specifically recognize the sites involved in activation of proteins of pharmacological importance (e.g., GHR). Once identified and characterized as regulators of target activity, these peptides may be used in high throughput screens to identify and provide information on small molecules which bind at these sites and, when dimerized, mimic the function of GH.

The present invention encompasses assays for identifying compounds that mimic the binding characteristics of growth hormone. Such compounds would serve as antagonists of growth hormone function. Dimers of such compounds would serve as growth hormone agonists.

The present invention also encompasses peptides (i.e., amino acid sequences) that compete with growth hormone for binding to growth hormone receptor. The disclosed peptides can be used in the assays of the invention to identify compounds that mimic growth hormone. In addition, such peptides can be used in kits and therapeutic compositions, as described in detail herein. The peptides of the invention may act as agonists or antagonists of growth hormone receptor. In the case of peptide antagonists, the amino acid sequences of these peptides can be linked, coupled, or combined to create dimer (e.g., homodimer or heterodimer) sequences that have agonist activity.

BRIEF DESCRIPTION OF THE FIGURES

FIG. 4 shows the results of analysis to determine the contribution of the FLAG (DYKD) sequence (SEQ ID NO:79) and cysteine residues for H5 (SEQ ID NO:8) to binding to rGHBP. Alanine replacement for single or multiple amino acids is represented by “a” and for cysteine by “X”.

FIG. 11A shows binding of bGH to rGHBP. FIG. 11B shows binding of bP#418 (SEQ ID NO:12) to rGHBP. FIG. 11C shows binding of bP#447 (SEQ ID NO: 11) to rGHBP.

FIG. 12A shows competition of bGH (2 nM) with GH. FIG. 12B shows competition of bGH (2 nM) with Mab2c3. FIG. 12C shows competition of bP#418 (SEQ ID NO:12; 300 nM) with GH. FIG. 12D shows competition of bP#418 (SEQ ID NO:12; 300 nM) with Mab2c3. FIG. 12E shows competition of bP#447 (SEQ ID NO:11; 300 nM) with GH. FIG. 12F shows competition of bP#447 (SEQ ID NO: 11; 300 nM) with Mab2c3.

FIG. 15 shows FIGS. 15A–C show the sequence of peptides from the secondary H5 library that bound to GHBP. Positions in bold were variable among the binders.

DETAILED DESCRIPTION OF THE INVENTION

Figure 1:
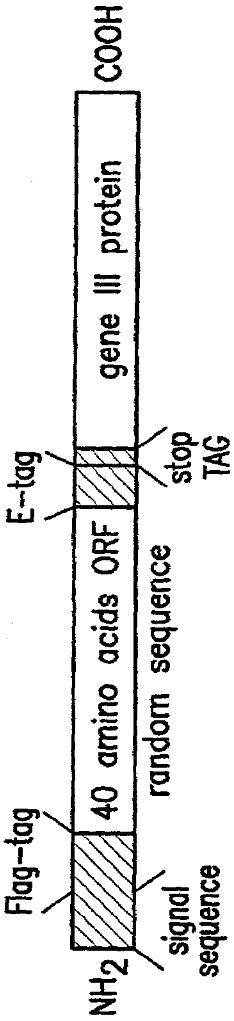
FIG. 1 shows a schematic diagram for the peptide library.

Assays have been developed for the purpose of identifying peptides or other compounds that bind to and dimerize two growth hormone receptor subunits. Such peptides or compounds would mimic the function of growth hormone, and would thus be useful as therapeutic agents. The assays are based on the discovery and identification of peptides that bind to a growth hormone receptor subunit (GHBP) and inhibit the binding of growth hormone to growth hormone receptor.

Randomly generated nucleic acid sequences were used to generate libraries of phage capable of expressing random peptides encoded by the nucleic acid sequences. The phage-displayed peptides were screened for binding to rGHBP and phage which express peptides that bind rGHBP were obtained. Certain peptides were determined to be capable of competitive inhibition of binding of growth hormone to rGHBP. These peptides thus mimic the binding characteristics of growth hormone, and can be used in assays to identify other compounds that inhibit the binding of the peptides to rGHBP.

The peptides of the present invention that bind to GHBP are artificial, i.e., non-naturally occurring, amino acid sequences. The disclosed peptides may be obtained through various means such as chemical synthesis, phage display, cleavage of proteins or polypeptides into fragments, or any means by which peptides may be made or obtained.

In accordance with the present invention, an in vitro competitive receptor-binding assay has been used as the basis of a High Throughput Screen (HTS) for small organic molecular replacements for GH. In this assay, occupation of the active site of rGHBP is quantified by Time Resolved Fluorometric Detection (TRFD). The TRFD assay format is well established, sensitive, and quantitative (Tompkins et al.). Generally, TRFD assays use streptavidin-labeled europium (saEu) to complex with biotinylated peptides (bP).

For this invention, saEu forms a ternary complex with bP and rGHBP (i.e., the rGHBP:bP:saEu complex). As described herein, the TRFD assay is performed using biotinylated GH (bGH) as bLigand. Biotinylated H5-mutant peptides bP#447 (SEQ ID NO:11) and bP#418 (SEQ ID NO:12) are also used as bLigand (see below). The TRFD assay described herein faithfully reports the competition of ligand binding to the active site of rGHR. To perform the TRFD assays, soluble rGHBP is attached to the surface of microtiter wells, then incubated with bP. Unbound bP is than washed away and (sa)Eu is added to complex with receptor bound bP. The rGHBP:bP bound (sa)Eu is then converted into its highly fluorescent state and detected by TRFD.

The present invention encompasses peptides (i.e., amino acid sequences) that bind to growth hormone receptor comprising the consensus sequence $CQX_1X_2X_3X_4X_5X_6PGWX_7X_8X_9WC$ (SEQ ID NO:4), wherein $X_1$ is S, R, T; N, H, or A; $X_2$ is L, W, or F; $X_3$ is G, A, V, P, Q, E, or R; $X_4$ is V, I, A, L, D, E, P, or F; $X_5$ is T, G, S, R, K, N, A, L, or W; $X_6$ is Y, W, F, or Q; $X_7$ is Y, W, F, or Q; $X_8$ is A, T, S, V, W, or D; and $X_9$ is G, A, S, or R. In another embodiment, the consensus sequence is $L_1CQS_4L_5G_6V_7T_8Y_9PGWL_{13}A_{14}G_{15}WCA_{18}$ (SEQ ID NO: 16), wherein $L_1$ is L or M; $S_4$ is S, R, T, N, or A; $L_5$ is L, W, or F; $G_6$ is G, A, V, P, Q, E, or R; $V_7$ is V, I, A, L, D, E, P, or F; $T_8$ is T, G, S, R, K, N, A, L, or W; $Y_9$ is Y, W, or F; $L_{13}$ is L, V, or I; $A_{14}$ is A, T, S, V, W, or D; $G_{15}$ is G or A; and $A_{18}$ is G, A, S, or R.

The invention also encompasses peptides that comprise the conserved amino acids of SEQ ID NO:2–3,5–8, 10–14, 16–78, and 82–84, but vary at one or more non-conserved positions of SEQ ID NO:2–3,5–8, 10–14, 16–78, and 82–84. For example, in the consensus sequence $CQX_1X_2X_3X_4X_5X_6PGWX_7X_8X_9WC$ (SEQ ID NO:4), residues $C_1$, $Q_2$, $P_9$, $G_{10}$, $W_{11}$, $W_{15}$, and $C_{16}$ are conserved, whereas residues $X_1$–$X_9$ are variable. Similarly, in the consensus sequence $L_1CQS_4L_5G_6V_7T_8Y_9PGWL_{13}A_{14}G_{15}WCA_{18}$ (SEQ ID NO:16), residues $C_2$, $Q_3$, $P_{10}$, $G_{11}$, $W_{12}$, $W_{16}$, and $C_{17}$ are conserved, whereas residues L1, $S_4$, $L_5$, $G_6$, $V_7$, $T_8$, $Y_9$, $L_{13}$, $A_{14}$, $G_{15}$, and $A_{18}$ are variable.

Hence, the instant application encompasses the amino acid sequences of SEQ ID NO:2–3,5–8, 10–14, 16–78, and 82–84, and amino acid sequences that are distinctive to the sequences of SEQ ID NO:2–3,5–8, 10–14, 16–78, and 82–84 due to a different combination of amino acids at the variable positions. In specific embodiments, the peptides that bind to growth hormone receptor comprise the sequence LCQRLGVGWPGWLSGWCAKK (SEQ ID NO:5); LCQSWQVTWPGWLAGWCAKK (SEQ ID NO:6); AQWWTTIGSNMFVLPGLRGCTFLPP MQCDREIRVFLVVH (SEQ ID NO:7); or any of the sequences of SEQ ID NOS:8, 11–14, 16–78, and 82–84.

The present invention further encompasses secondary peptide libraries. The peptide sequences provided by this invention can be used to design secondary peptide libraries, which are derived from the peptide sequences, and include members that bind to growth hormone receptor. Such libraries can be used to identify sequence variants that increase or modulate the binding of the original peptide to growth hormone receptor, as described in detail herein.

Library construction and other molecular biology techniques used in accordance with this invention are well-known in the art. Such techniques are taught herein and in references such as Sambrook et al., 1989, *Molecular Cloning, A Laboratory Manual*, 2d ed., Cold Spring Harbor Laboratory Press, Cold Spring Harbor, N.Y., 1989; and F. M. Ausubel et al. (eds), 1995, *Current Protocols in Molecular Biology*, John Wiley and Sons, Inc., New York, N.Y.

The present invention also encompasses pharmaceutical compositions comprising the peptides disclosed herein. Such compositions include one or more of the peptides along with a physiologically acceptable carrier, excipient, or diluent. Suitable excipients are, for example, water, saline, dextrose, glycerol, ethanol, or the like and combinations thereof. In specific embodiments, the composition can contain minor amounts of auxiliary substances such as wetting or emulsifying agents, pH-buffering agents, which enhance the effectiveness of the active ingredient (i.e., peptide).

Pharmaceutical compositions in accordance with the invention may be developed as treatments for dwarfism or other diseases associated with a decreased response or production of growth hormone. The pharmaceutical compositions can be administered systemically by oral or parenteral routes. Non-limiting parenteral routes of administration include subcutaneous, intramuscular, intraperitoneal, intravenous, transdermal, inhalation, intranasal, intra-arterial, intrathecal, enteral, sublingual, or rectal. Due to the labile nature of the amino acid sequences parenteral administration is preferred. Formulations for administration include aerosols for nasal or bronchial absorption; suspensions for intravenous, intramuscular, intrasternal or subcutaneous, injection; and compounds for oral administration.

Further guidance in preparing pharmaceutical formulations can be found in Gilman et al. (eds), 1990, *Goodman and Gilman's: The Pharmacological Basis of Therapeutics*, 8th ed., Pergamon Press; and *Remington's Pharmaceutical Sciences*, 17th ed., 1990, Mack Publishing Co., Easton, Pa.; Avis et al. (eds), 1993, *Pharmaceutical Dosage Forms: Parenteral Medications*, Dekker, New York; Lieberman et al. (eds), 1990, *Pharmaceutical Dosage Forms: Disperse Systems*, Dekker, New York.

The present invention further encompasses methods for interfering with the binding between growth hormone and growth hormone receptor. These methods comprise administering an effective amount of a peptide that is able to disrupt or prevent the binding between growth hormone and growth hormone receptor or a functional peptide analogue thereof.

Also encompassed by the present invention are kits for identifying compounds that bind to growth hormone receptor. In accordance with the present invention, the growth hormone receptor binding assays disclosed herein can be used in conjunction with kits comprising growth hormone binding protein and one or more growth hormone receptor binding peptides (i.e., amino acid sequences). In one embodiment, these kits comprise GHBP and a growth hormone receptor binding peptide as separate constituents. The GHBP is used to isolate a binding component, and the growth hormone receptor binding peptide is used to compete with the component for binding to GHBP.

Alternatively, kits of the invention comprise a complex of GHBP and a growth hormone receptor binding peptide. This complex is used to isolate a binding component that can compete with the growth hormone receptor binding peptide for binding to GHBP. The peptide and receptor components of the kit may be labeled (e.g., by radioisotopes, fluorescent molecules, chemiluminescent molecules, enzymes or other labels), or may be unlabeled and labeling reagents may be provided. The kits may also contain peripheral reagents such as buffers, stabilizers, etc. Instructions for use can also be included.

GHR, GHBP, or the growth hormone receptor binding peptides disclosed herein may be modified with a label capable of providing a detectable signal, either directly or indirectly. Fluorescent labels include, for example, Cy™3, Cy™5, Alexa, BODIPY, fluorescein (e.g., Fluor X, DTAF, and FITC), rhodamine (e.g., TRITC), auramine, Texas Red, AMCA blue, and Lucifer Yellow. Preferred isotope labels include $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}$ Re. Preferred enzyme labels include peroxidase, β-glucuronidase, β-D-glucosidase, P-D-galactosidase, urease, glucose oxidase plus peroxidase, and alkaline phosphatase (see, e.g., U.S. Pat. Nos. 3,654,090; 3,850,752 and 4,016,043). Enzymes can be conjugated by reaction with bridging molecules such as carbodiimides, diisocyanates, glutaraldehyde, and the like. Enzyme labels can be detected visually, or measured by calorimetric, spectrophotometric, fluorospectrophotometric, amperometric, or gasometric techniques. Other labeling systems, such as avidin/biotin, Tyramide Signal Amplification (TSA™), are known in the art, and are commercially available (see, e.g., ABC kit, Vector Laboratories, Inc., Burlingame, Calif.; NEN® Life Science Products, Inc., Boston, Mass.).

GHR, GHBP, or the peptides of the invention can also be modified with sequence tags (e.g., Flag-tag, E-tag, 6×-His, c-myc, haemagglutinin (HA), GLU-GLU, etc.), protein tags (e.g., glutathione-S-transferase (GST), green fluorescent protein (GFP), and maltose binding protein (MBP), etc.), or amino acids, such as one or more lysines. These sequences can be added to the peptides of the invention (e.g., at the N-terminal or C-terminal ends) as described herein, or in accordance with other well-established techniques. In particular, sequence or protein tags can be used for peptide purification or localization. Lysines can be used to increase peptide solubility or to allow for biotinylation. Typically, the addition or deletion of such sequences will not affect peptide binding to GHR or GHBP. Accordingly, amino acid residues located at the carboxy and amino terminal regions of the consensus motifs described below, which comprise sequence tags (e.g., Flag-tags or E-tags), or which contain amino acid residues that are not associated with a strong preference for a particular amino acid, may optionally be deleted providing for truncated sequences. Certain amino acids (e.g., C-terminal or N-terminal residues) such as lysine which promote the stability or biotinylation of the amino acids sequences may be deleted depending on the use of the sequence, as for example, expression of the sequence as part of a larger sequence which is soluble, or linked to a solid support. Notably, the peptides, peptide libraries, kits, methods, and compositions of the invention can be used in conjunction with mammalian GHR or GHBP, including but not limited to, human, rat, and bovine GHR or GHBP.

As known by those in the art, obtaining mimetics to a known pharmaceutically active compound is an established approach to the development of pharmaceuticals based on a "lead" compound. This may be desirable where the active compound is difficult or expensive to synthesize or where it is unsuitable for a particular method of administration, e.g. peptides are unsuitable active agents for oral compositions as they tend to be quickly degraded by proteases in the alimentary canal. Mimetic design, synthesis, and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modeled according to its physical properties, e.g. stereochemistry, bonding, size, and/or charge, using data from a range of sources, e.g. spectroscopic techniques, X-ray diffraction data, and NMR. Computational analysis, similarity mapping (which models the charge and/or volume of a pharmacophore, rather than the bonding between atoms) and other techniques can be used in this modeling process. In an alternate approach, the three dimensional structure of the ligand and its binding partner are modeled. This can be especially useful where the ligand and/or binding partner change conformation on binding, allowing the model to take account of this in the design of the mimetic.

A template molecule is then selected onto which chemical groups that mimic the pharmacophore can be grafted. The template molecule and the chemical groups grafted on to it can conveniently be selected so that the mimetic is easy to synthesis, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimization or modification can then be carried out to arrive at one or more final mimetics for in vivo or clinical testing.

In order to identify compounds that are useful in the above-described methods, compounds may be screened for interference of the growth hormone/growth hormone receptor interaction. Suitable screening methods would be based upon observations with regard to compounds that interfere with the binding between peptides that comprise or represent the binding site of a receptor. Such methods include, but are not limited to, immunoassay techniques such as radioimmunoassay (RIA), enzyme linked immunoadsorbent assay (ELISA), and radioligand binding assays which are well known in the art.

Peptides that bind specifically to different forms of GHBP (e.g., 'hu'-specific peptides) allow screening for a peptide-based 3D pharmacophore structure via standard NMR analysis. Such a pharmacophore, on its own or after comparison with 3D pharmacophores obtained for the H5-related rat GHBP binding peptides (see below), allows the identification of residues required for species-specific binding to GHR. The 'hu'-specific pharmacophore, in turn, allows development of computer-based screening efforts to identify small organic molecules from a chemical library that are predicted to bind to 'hu' GHR. Chemical and/or recombinant synthesis can be used to make sufficient soluble peptide (free or as fusion with some carrier protein) for testing agonist and antagonist activities.

In addition, 'hu'-specific peptides and 'hu' GHBP can be used to establish a peptide-receptor pair to be used in a site-directed competition binding assay. In this assay, 'hu' GHBP can be used as one member of the pair, with the 'hu'-specific peptide as the other member. Labeling of each member, and detection of pair formation, using either member in radioactive or nonradioactive labeled forms, is possible by a variety of methods known to those skilled in the art. For example, many types of competition binding assays can be used. Such assays would enable high throughput screening for small organic molecules from a chemical library that bind to 'hu' GHBP. Dimerization of positive small molecules would provide a bivalent small molecule with human GH activity.

Furthermore, one may synthetically or recombinantly, modify the sequence of the 'hu'-specific peptide to derive a secondary combinatorial library. Secondary libraries can be used to determine the residues required for phage-displayed binding to 'hu' GHBP, and provide a consensus sequence for 'hu' GHBP binding. Amino acid alterations, single or combinatorial, can be made following any number of mutational schemes. Such schemes may be similar to that used for the secondary H5 library (see below), or other mutational analyses known to those of skill in the art. A secondary library of mutagenized 'hu'-specific peptide expressed in the RAPIDLIB format (see below), or other combinatorial phage or protein display formats, can be panned against 'hu' GHBP for several rounds (e.g., up to 5 rounds). Following this, individual clones can be picked and analyzed for specific binding to 'hu' GHBP, which can be competed or blocked by human GH. In this fashion additional and improved 'hu' GHBP binders, consensus sequences, and smaller amino acid sequences can be obtained. This can lead to large-scale synthesis of the 'hu'-specific peptide. Recombinant expression vectors can be used for production of necessary quantities of larger peptides (e.g., greater than 40 amino acids). Such peptides can also be used for structural determinations to improve on the pharmacophore model associated with active site GH receptor binding.

EXAMPLES

The examples as set forth herein are meant to exemplify the various aspects of this invention and are not intended to limit the invention in any way.

Example 1

Construction of Phage Library

DNA fragments coding for peptides containing 40 random amino acids were generated in the following manner. A 145 base oligonucleotide was synthesized to contain the sequence $(NNK)_{40}$, where N=A, C, T, or G, and K=G or T. This oligonucleotide was used as the template in PCR amplification along with two shorter oligo primers, both of which were biotinylated at their 5' ends. The resulting 190 bp product was purified and concentrated with QIAquick spin columns (QIAGEN), then digested with Sfi I and Not I restriction enzymes. Streptavidin-agarose (GIBCO) was added to the digestion mixture to remove the cleaved ends of the PCR product as well as any uncut DNA. The resulting 150 bp fragment was again purified over QIAquick spin columns.

The phagemid pCANTAB5E (Pharmacia) was digested with Sfi I and Not I, followed by phosphatase treatment. The digested DNA was purified using a 1% agarose gel followed by QIAEX II (QIAGEN). The vector and insert were ligated overnight at 15° C. The ligation product was purified using QIAquick spin columns (QIAGEN) and electroporations were performed at 1500 volts in an electroporation cuvette (0.1 mm gap; 0.5 ml volume) containing 12.5 μg of DNA and 500 μl of TG1 electrocompetent cells. Immediately after the pulse, 12.5 ml of pre-warmed (40° C.) 2xYT medium containing 2% glucose (2xYT-G) was added and the transformants were grown at 37° C. for 1 hr. Cell transformants were pooled, the volume measured, and an aliquot was plated onto 2xYT-G containing 100 μg/ml ampicillin (2xYT-AG) plates to determine the total number of transformants. Sequence analysis of randomly selected clones indicated that 54% of all clones were in-frame (Mandecki et al., 1997).

Preparation of Electrocompetent Cells

To prepare electrocompetent cells an overnight culture of *E. coli* TG1 cells (F' traD36 $lacI^q$ Δ(lacZ)M15 proA+B+/supE Δ(hsdM-mcrB)5 $r_k$-$M_k$-McrB-) thi Δ(lac-proAB) was diluted to an $O.D._{600}$=0.05–0.1 in 500 ml 2xYT, then grown at 37° C. in 4 liter Ehrlenmyer flasks to an $O.D._{600}$=0.5–0.6. The culture was poured into pre-chilled centrifuge bottles and incubated on ice for 30 min prior to centrifugation at 2000×g for 30 min (2° C.). The supernatant was poured off, and the cell pellet was resuspended in a total of 400 ml of ice cold sterile distilled water. The process of centrifugation and resuspension was repeated two more times. After the last centrifugation, the pellet was resuspended in a total of 25 ml of ice cold water containing 10% glycerol. The cell suspension was transferred to pre-chilled 35 ml centrifuge bottles, and was then pelleted at 2000×g for 10 min at 4° C. The cells were then suspended in 0.3 ml of the same 10% glycerol solution, aliquotted into smaller tubes, and snap-frozen on dry ice. The aliquots were stored at −80° C.

To amplify the library, the transformants were inoculated into four liters of 2xYT-AG medium and allowed to grow until the $A_{600}$ increased approximately 400 times. The cells were pelleted by centrifugation at 3000×g for 20 min, then resuspended in 40 ml 2xYT-AG to which glycerol was added to a final concentration of 8%. The library was stored at −80° C.

This process was carried out using the standard phage preparation protocol (above) with the following changes. Five individual recombinant cell libraries, with a total diversity of $1.6\times10^{10}$, were combined and grown to $O.D._{600}$=0.5 in 2xYT-AG at 30° C. with shaking (250 rpm). Helper phage (M13K07) was then added (MOI=15), and the cells were incubated for 30 min at 37° C. without shaking, followed by 30 min at 37° C. with shaking (250 rpm). The precipitated phage pellet was resuspended in phosphate-buffered saline (1/100 of the initial culture volume) and passed through a 0.45 μm filter. The phage were titered by infecting TG1 cells. The phage titer was $4\times10^{13}$ cfu/ml.

To prepare the phage, bacterial cells containing phagemid were grown to $O.D._{600}$=0.5 in 2xYT-AG (yeast tryptone medium containing 100 mg/ml ampicillin and 2% glucose) at 37° C. with shaking (250 rpm). M13K07 helper phage was then added (MOI (multiplicity of infection)=15), and the cells were incubated for 30 min at 37° C. with gentle shaking. Following infection, cells were pelleted and the supernatant containing the helper phage was discarded. The cell pellet was resuspended in the initial culture volume of 2xYT-A (no glucose) containing 50 mg/ml kanamycin and grown overnight at 30° C. with shaking (250 rpm). The cells from the overnight culture pelleted at 3000×g for 30 min at 4° C. and the supernatant containing the phage was recovered. The solution was adjusted to 4% PEG, 500 mM NaCl and chilled on ice for 1 hr. The precipitated phage were pelleted by centrifugation at 10,000×g for 30 min. The pellet was resuspended in PBS containing 2% non-fat dried milk (MPBS).

A standard method was used to coat and block all microtiter plates. The target protein of interest was diluted to 1 mg/ml in 50 mM sodium carbonate buffer, pH 9.5. One hundred microliters of this solution was added to an appropriate number of wells in a 96-well microtiter plate (MaxiSorp plates, Nunc) and incubated overnight at 4° C. Wells were then blocked with MPBS at room temperature for 1 hr.

Example 2

Expression and Purification of Growth Hormone Binding Protein

Construction of the humanized GHBP

DNA encoding the rat GHBP was used as a template. A total of three PCR reactions were performed. The first of these amplified the DNA encoding amino acids 1–48 of GHBP. The 3' oligo used for this reaction encoded the mutation L43R (CTG→AGA). The second PCR reaction amplified the DNA encoding amino acids 38–260 of GHBP. The 5' oligo used for this reaction was complementary to the 3' oligo used for the first reaction, and also encoded the L43R mutation. Both PCR products were purified using QIAquik spin columns (QIAGEN), then mixed in equimolar amounts and reamplified using the 5' oligo from the first reaction and the 3' oligo from the second reaction. This resulting full-length DNA was again purified over a QIAquik spin column, then sequenced to verify the changed sequence. Expression and purification of the humanized GHBP were done essentially as described above.

An overnight culture was diluted 1:100 into 1 liter of 2xYT media containing 100 μg/ml ampicillin. This culture was grown to O.D.$_{-600}$=0.6, then induced with 1 mM IPTG for 3 hr. The cells were pelleted, and the pellet was resuspended in 60 ml of sonication buffer (50 mM Tris-HCl, pH 8.0; 150 mM NaCl; 1 mM PMSF). After sonication, the material was centrifuged at 4000 rpm for 20 min at 4° C. The resulting pellet was re-sonicated and centrifuged as above. This pellet was then resuspended in extraction buffer (8M urea; 50 mM Tris-HCl, pH 8.0) and incubated at room temperature for 4 hr with gentle rotation. The material was then centrifuged at 16,000 rpm for 20 min, and the resulting supernatant was filtered through a 0.45 μm filter. The 6×-His tagged material was loaded onto a Ni-NTA column previously equilibrated with running buffer (PBS and 8M urea). The column was washed with 10 column volumes of running buffer containing 0.5 mM imidazole. The protein was eluted with running buffer containing 150 mM imidazole. Fractions were dialyzed overnight against PBS containing 0.2 mM PMSF. The dialyzed sample was then clarified by centrifugation at 14,000 rpm for 10 min.

Example 3

Panning Growth Hormone Binding Protein

The peptide library was panned against soluble rGHBP. The microtiter plates were then coated with MAb 4.3 and then blocked with milk. MAb 4.3 is a non-neutralizing murine IgG specific for the carboxyl terminal tail of GHBP that results from alternative splicing of the mRNA. Soluble rGHBP was added next and after 2 hrs unbound rGHBP was removed by washing, and the standard panning procedure was initiated, with eight wells used for each round of panning. The phage were incubated with MPBS for 30 min at room temperature, then 100 μl was added to each well.

For the first round, the input phage titer was $4\times10^{13}$ cfu/ml. For rounds 2 and 3, the input phage titer was approximately $10^{11}$ cfu/ml. Phage were allowed to bind for 2 to 3 hr at room temperature. The wells were then quickly washed 13 times with 200 μl/well of MPBS. Bound phage were eluted by incubation with 100 μl/well of 20 mM glycine-HCl, pH 2.2 for 30 seconds. The resulting solution was then neutralized with Tris-HCl, pH 8.0. Log phase TG1 cells were infected with the eluted phage, then plated onto two 20 cm×20 cm plates containing 2xYT-AG. The plates were incubated at 30° C. overnight. The next morning, cells were removed by scraping and stored in 10% glycerol at −80° C. For subsequent rounds of affinity enrichment, cells from these frozen stocks were grown and phage were prepared as described above. A total of 72 clones were picked at random from the second and third rounds of panning and screened for binding activity.

Example 4

ELISA Analyses of Phage

For analysis of individual clones, colonies were picked and phage prepared as described above. Microtiter wells were coated and blocked as described above. Wells were coated with either rGHBP or a control IgG MAb. Phage resuspended in MPBS were added to duplicate wells (100 μl/well) and incubated at room temperature for 1 hr. The phage solution was then removed, and the wells were washed three times with PBS at room temperature. Anti-M13 antibody conjugated to horseradish peroxidase (Pharmacia Biotech) was diluted 1:3000 in MPBS and added to each well (100 μl/well). Incubation was for another hour at room temperature, followed by PBS washes as described. Color was developed by addition of ABTS solution (100 μl/well; Boehringer). Color development was stopped by adjusting each well to 0.5% SDS. Plates were analyzed at 405 nm using a SpectraMax 340 plate reader (Molecular Devices) and SoftMax Pro software. Data points were averaged after subtraction of appropriate blanks. A clone was considered "positive" if the $A_{405}$ of the well was >2-fold over background.

Figure 3:
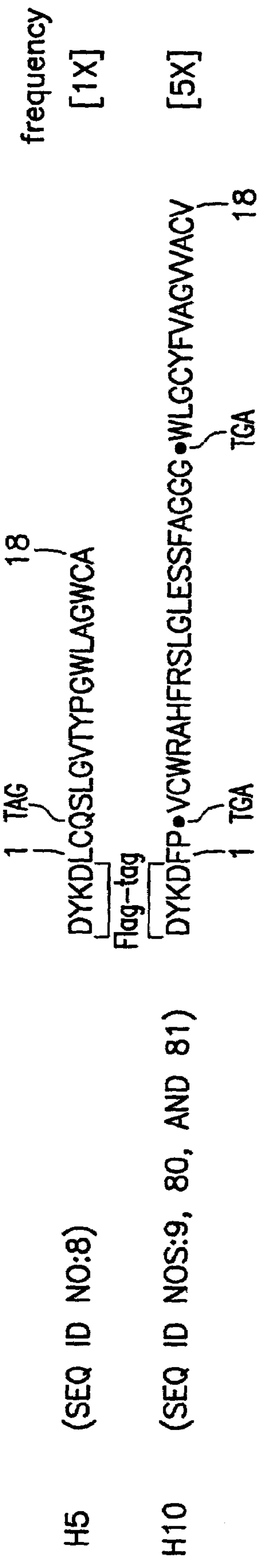
FIG. 3 shows the sequence of H5 (SEQ ID NO:8) and H10 clones (SEQ ID NOS:9, 80, 81). Nonsense codon TAG is suppressed as Q; TGA has no identified suppressor. x=number of times a clone appeared in Round 3 panning (out of 72 total clones).

Five Round 3 clones were positive as judged by binding to rGHBP (FIG. 2A) and DNA sequence analyses showed that these were comprised of two distinct clones (FIG. 3). The first clone, GHBP-H5 (H5; SEQ ID NO:8), has an open reading frame (ORF) while the other, GHBP-H10(H10; SEQ ID NOS:9, 80, and 81) does not have an ORF and is referred to as a frame shifted clone.

For $IC_{50}$ determinations in a competitive ELISA, microtiter plates were coated with GHBP and blocked as described. Phage were prepared as described. Prior to addition of phage to plates, H5 peptide (SEQ ID NO:8) or a control peptide (SEQ ID NO:10) was diluted in PBS and added to duplicate wells (100 μl/well). After incubation for 1 hr at room temperature, the prepared phage were added to each well (100 μl/well) without removing the peptide solution. After incubation for another hour at room temperature, the wells were washed and the color developed as described above.

Figure 2B:
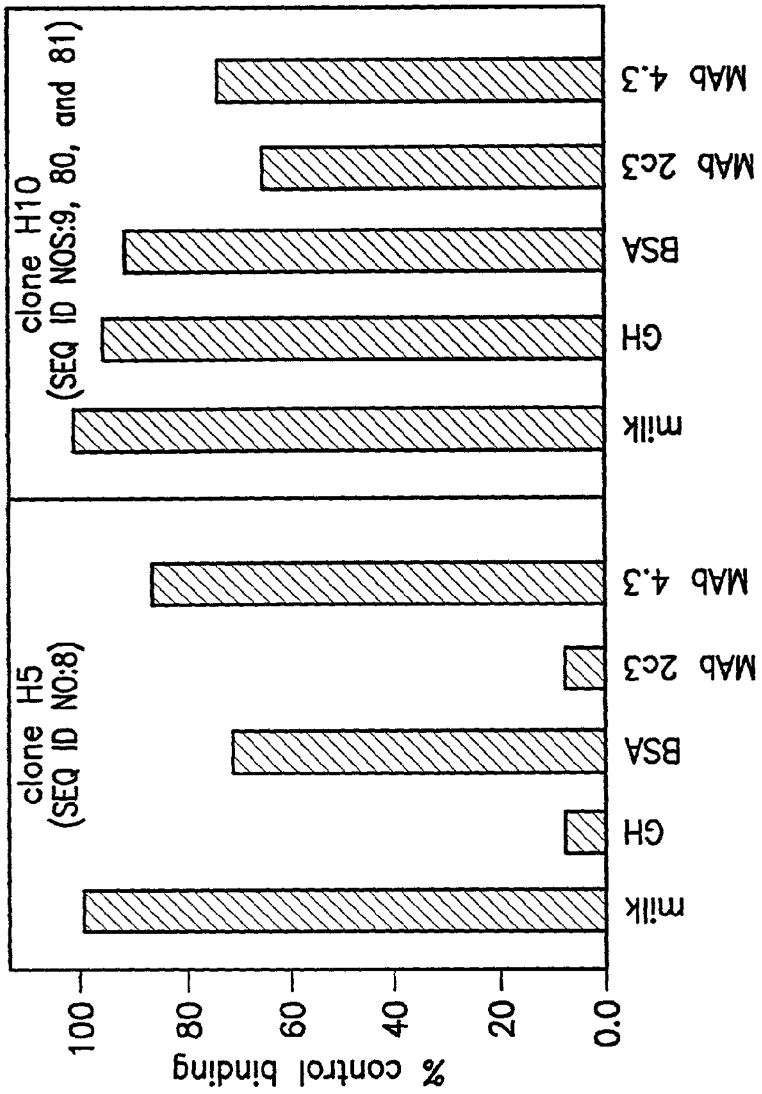
FIG. 2B shows the results of ELISA analysis demonstrating competition of H5 (SEQ ID NO:8) and H10 peptide (SEQ ID NOS:9, 80, 81) mediated phage binding to rGHBP.
Figure 2A:
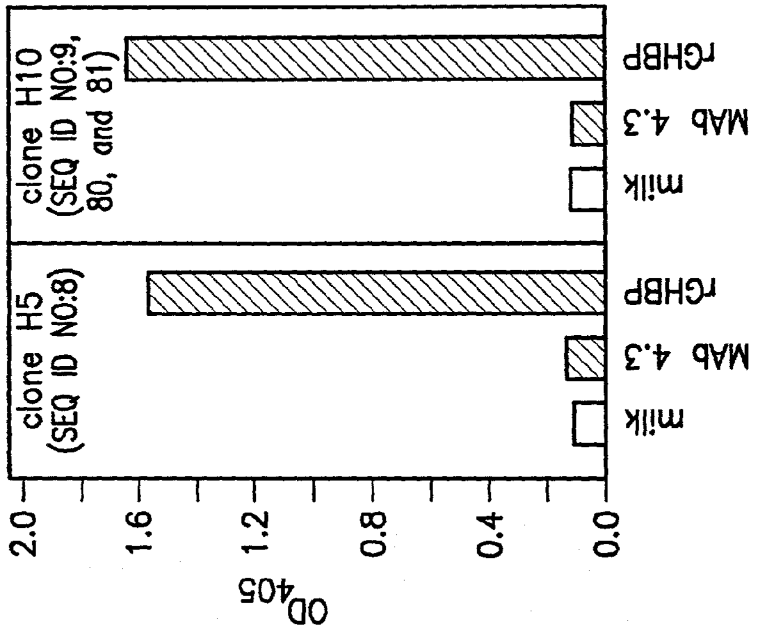
FIG. 2A shows the results of ELISA analysis demonstrating H5 (SEQ ID NO:8) and H10 peptide (SEQ ID NOS:9, 80, 81) mediated phage binding to rGHBP.

These clones were next analyzed for binding to the receptor's active sites (FIG. 2B). Competitions of phage binding were done both with the cognate ligand (i.e., GH) and with a specific target-neutralizing MAb 2C3 (Wang, B. S., et al. *Mol. Cellular Endocrinology, vol.* 116, p. 223–226, 1996). The binding of H5 (SEQ ID NO:8) was blocked both by GH and by MAb 2C3. The second positive rGHBP clone, H10 (SEQ ID NOS:9, 80, and 81), a shifted clone, was not blocked by either GH or MAb 2C3 (FIG. 2B).

To determine the rank order for phage peptides, the rGHBP (25 μg/ml) was immobilized onto a CM-5 (BIAcore) sensor chip using amino coupling chemistry and the manufacturer's recommended protocol. The final surface density was 1000 RU. A monoclonal antibody was immobilized onto another flow cell as a control surface. Phage were directly injected (30–100 μl) with a buffer flow rate of 1 μl/min. Background binding to the control surface was subtracted prior to further analysis.

Example 5

Secondary Phage Library Based on Clone H5 (SEQ ID NO:8)

Once the H5 peptide (herein referred to as wild type; H5WT; SEQ ID NO:8) was determined to bind the active site of rGHBP, the peptide's properties were modified using mutagenesis. The goal was to bring the affinity into a range that would allow the peptide to be used in a receptor binding assay and tested in a cell based assay for activity. Before selecting residues for mutagenesis, it was determined that DYKD (SEQ ID NO:79) did not play any role in binding but that both cysteines were essential.

Figure 4A:
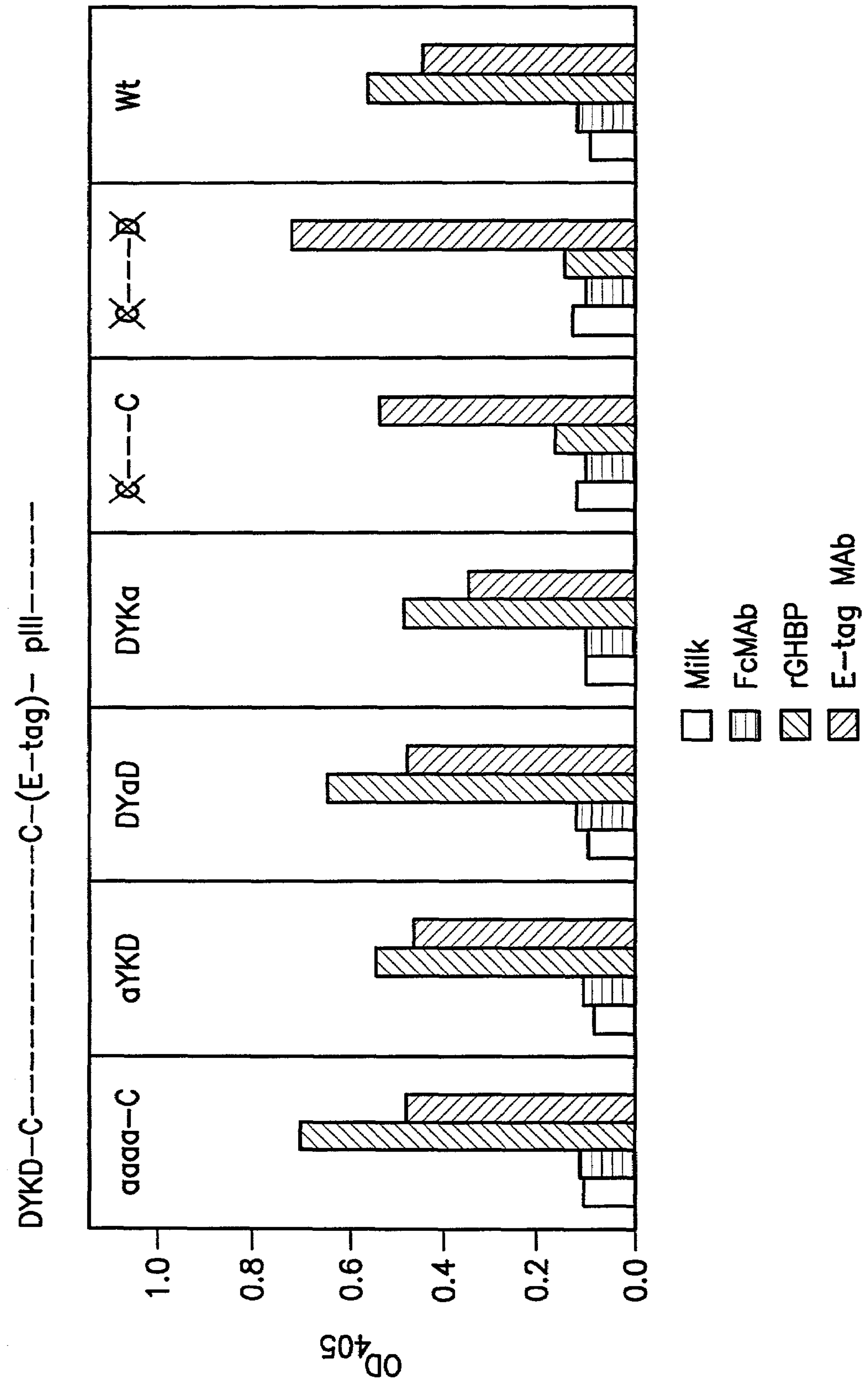
FIG. 4A illustrates the binding of wild-type (WT) and mutant phage on wells coated with milk (2%), FcMAb (100 ng/well), rGHBP (100 ng/well), or MAb specific for the E-tag epitope (100 ng/well).
Figure 4B:
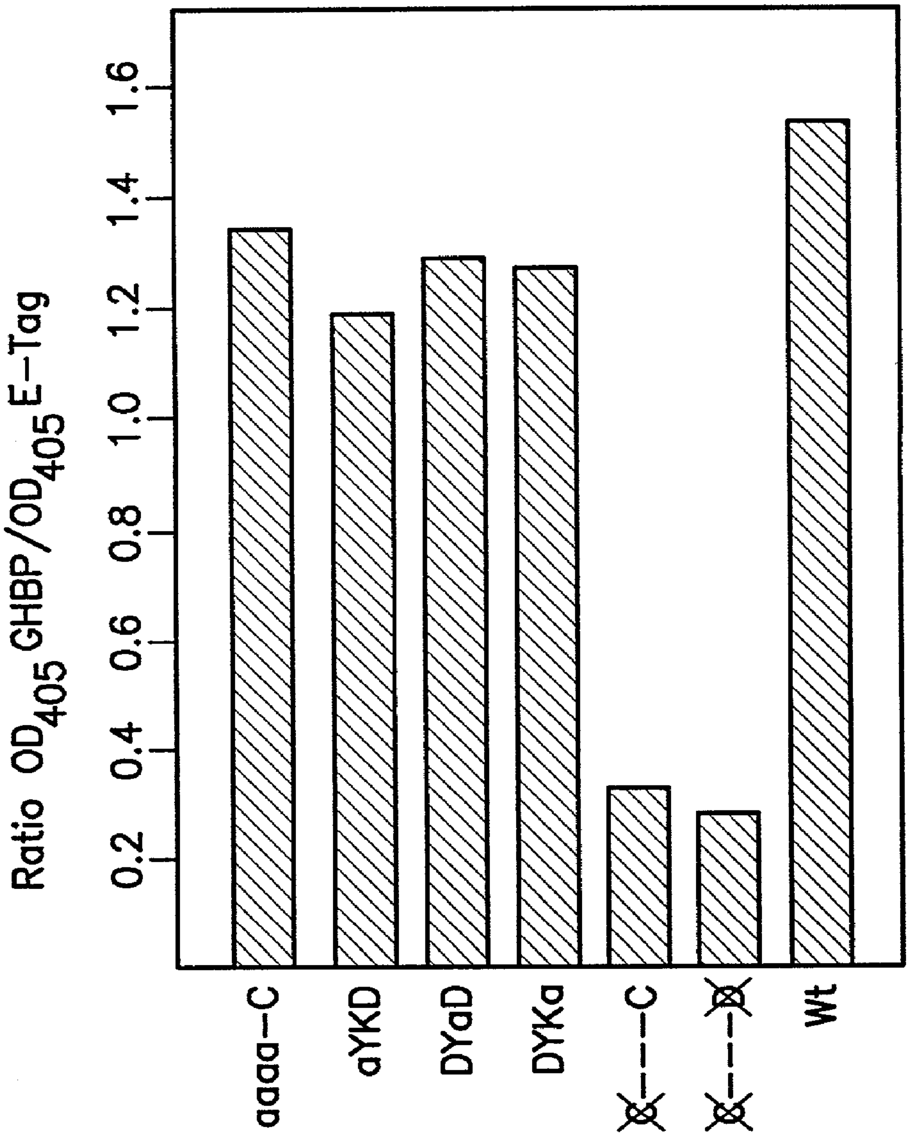
FIG. 4B illustrates the ratio of mutant phage binding to rGHBP versus anti-E-tag MAb coated wells.

For this analysis, phage were input at $10^{10}$/well. Wild type (WT) and mutant phage were tested on wells coated with milk (2%), FcMAb (100 ng/well), rGHBP (100 ng/well), or MAb specific for the E-tag epitope (100 ng/well) (FIG. 4A). Detection with HRP-anti M13 phage antibody was done as described. The ratio of phage binding to rGHBP versus anti-E-tag MAb coated wells with H5 mutants is shown in FIG. 4B. In FIG. 4, alanine replacement for single or multiple amino acid is represented by "a" and for cysteine by "X". It was concluded that the DYKD (SEQ ID NO:79) residues were not important for GHBP binding. represented by "a" and for cysteine by "X". It was concluded that the DYKD (SEQ ID NO:79) residues were not important for GHBP binding.

Among several available mutagenesis methods, one was chosen based on gene synthesis and phage display. In this method a library of doped oligonucleotides carrying several mutations in any single DNA molecule was used to obtain a pool of mutant genes that were phage displayed. This method allowed encoding of both the original H5WT peptide (SEQ ID NO:8) as control as well as versions containing high numbers of mutations per peptide in a very large library (>$10^{10}$).

Figure 6:
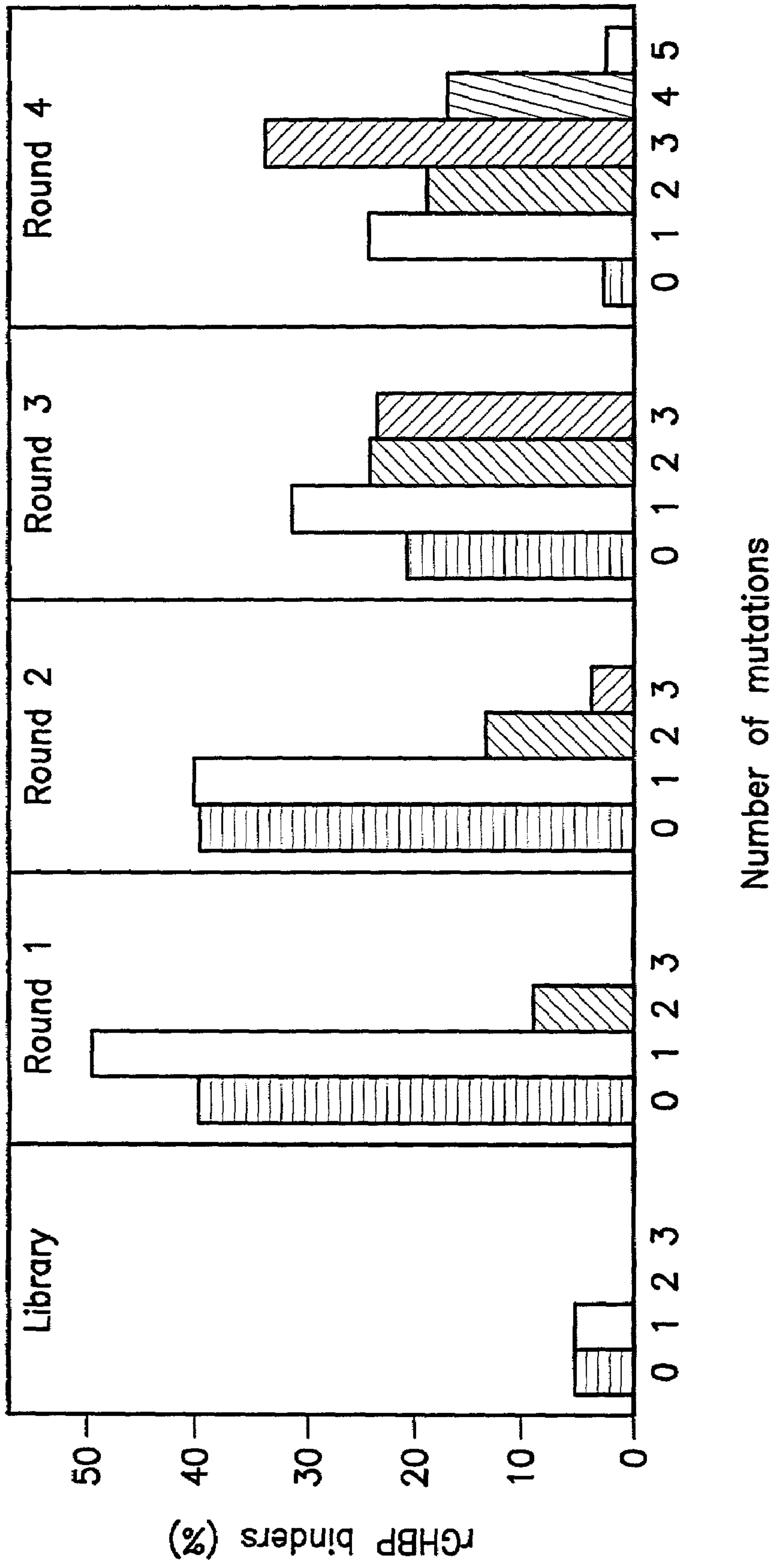
FIG. 6 shows the distribution of the number of amino acid mutations in peptides that bind rGHBP from the secondary H5 library

The H5 secondary mutant library was designed to contain an average of four mutations per peptide. The number of possible mutant H5 peptide sequences having four mutations was $1.0\times10^{10}$ and was equivalent to the actual size of the secondary phage library. Sequence analysis indicated that of these peptides 30% had 3–4 mutations, 33% had 1–2 mutations, and 32% had 5–6 mutations. There was also a small percentage with 7–8 mutations, and the H5WT sequence (SEQ ID NO:8) occurred at a frequency of about 5% (FIG. 6, Round 0).

An oligonucleotide based on the DNA sequence encoding the H5WT peptide (SEQ ID NO:8) was synthesized. The sequence of the oligonucleotide was: 5'CTACAAAGACCT-GTGTTAGAGTTTGGGGGTTACGTATCCGGGTTGGTT GGCGGGGTGGTGTGCGGCGGCCGCAGTGTGA3' (SEQ ID NO: 1). The underlined base positions were synthesized as mixtures of four nucleosides as follows:

A=90% A; 3.3% C, 3.3% G; and 3.3% T

C=3.3% C; 90% C, 3.3% G; and 3.3% T

G=3.3% C, 3.3% C; 90% G; and 3.3% T

T=3.3% C, 3.3% C, 3.3% G; and 90% T

Using this oligo as a template, the H5 secondary library was constructed, electroporated, amplified, and rescued essentially as described for the original peptide library. The final diversity of this secondary library was ~$10^{10}$.

More than 50 randomly picked clones from the secondary library (Round 0, before panning) were rescued. Phage were assayed in an ELISA for binding to the anti-E-tag MAb, as well as for binding to the rGHBP. Binding to anti-E-tag MAb was used as an indicator of expression of displayed peptides on phage surfaces. The results (FIG. 6) showed that although most of the clones displayed a peptide, i.e., were positive for anti-E-tag MAb, only about 1% bound to rGHBP. This indicated that the most common outcome of random mutagenesis was the loss of rGHBP affinity. Nevertheless, some mutants had retained their binding properties and some had improved affinities (see below).

Example 6

Panning with the Secondary H5 Library

Approximately 100 clones from each round of panning were analyzed in a phage ELISA to identify the clones that bind to the receptor. The positive clones were subjected to DNA sequencing and protein sequence comparison. FIG. 15 provides a listing of different sequences obtained from each round of panning. Data on the right are the number of individual clones found to bind to rGHBP which were isolated from Round 1–4 of panning. Total clones analyzed in round 1–4 respectively were 21, 38, 28, and 40. Wells were coated with rGHBP (100 ng/well) and blocked as described. FIG. 6 shows the frequency of mutations found among positive binding in each of the panning rounds. The results indicated that binders from later rounds of panning contained more mutations than those from earlier rounds. Some binders were present in multiple copies. This was the most striking in round 4.

Certain mutations occurred frequently in the rGHBP binders. The residues highly permissible to change among binders were $S_4$-$L_5$-$G_6$-$V_7$-$T_8$-$Y_9$, as well as $A_{14}$. Rarer mutations were also observed at $L_1$, $L_5$, $G_{15}$, and $A_{18}$. As expected, the two cysteine residues, $C_2$ and $C_{17}$, were absolutely conserved. The two residues just internal to the two C residues, $Q_3$ and $W_{16}$, and the triplet $P_{10}$-$G_{11}$-$W_{12}$ were also absolutely conserved. Three point mutations stood out as occurring more than 20 times in the clones sequenced. These were: $S_4$ to R, $T_8$ to G, and $Y_9$ to W. One of the two clones observed most often (8 times) had these three mutations and no other mutations. The other clone that was observed 8 times had a single point mutation, $Y_9$ to W. This was one of the three mutations seen most frequently. Two other clones were found 5 times each. They carried subsets of the three dominant point mutations, either $T_8$ to G and $Y_9$ to W; or $S_4$ to R and $Y_9$ to W. These data were suggestive of the involvement of the newly mutated residues in binding to the receptor. The results are summarized in FIG. 7, which also gives a consensus RGHBP binding sequence.

Figure 8:
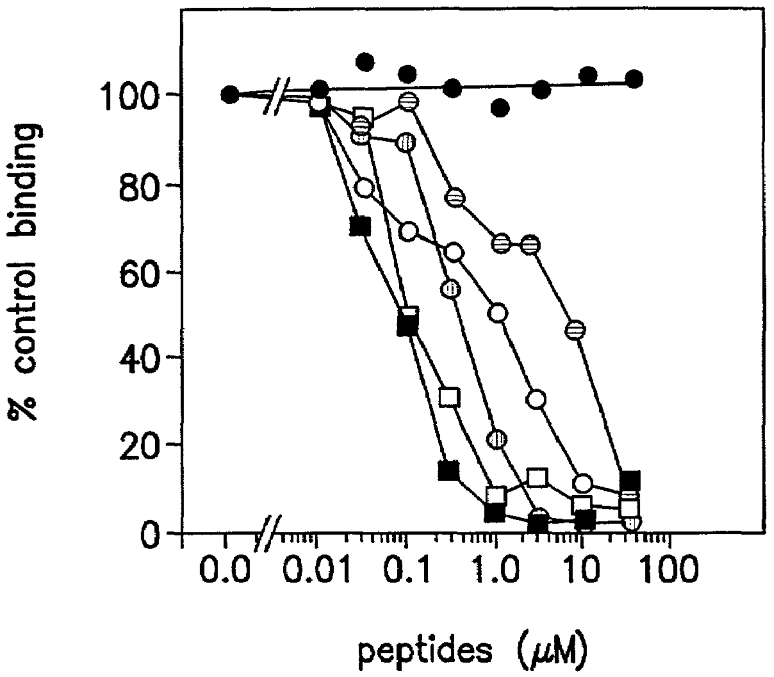
FIG. 8 shows competition of H5 (SEQ ID NO:8) phage binding to rGHBP by synthetic peptides. Wells were coated with rGHBP (100 ng/well) and blocked as described. Peptides were added 1 hr prior to addition of H5 (SEQ ID NO:8) phage ($10^{10}$/well) and incubation continued for 1 hr. The peptides included two lysine residues added to the C-terminus of the sequence shown. Phage binding was detected with HRP-anti M13 phage antibody. Number and sequence of competing peptides are detailed on the right of figure. Control binding=binding in absence of peptide.

The H5WT (SEQ ID NO:8) and a randomly scrambled H5WT control (SEQ ID NO:10) were obtained by chemical synthesis. The mutant phage from different rounds of panning were first compared for affinity for the rGHBP in a competition ELISA in which the $IC_{50}$ of synthetic H5 (SEQ ID NO:8) was determined for each. Based on these results, 12 other peptides were selected for chemical synthesis. All synthetic peptides were then tested as competitors of H5WT (SEQ ID NO:8) phage binding as shown in FIG. 8, and rank ordered as to $IC_{50}$. The highest-ranked sequences most often contained combinations of the most frequently observed point mutations (i.e., $S_4$ to R, $T_8$ to G, and $Y_9$ to W). The exception was clone 418 (SEQ ID NO:12) which carried the $Y_9$ to W mutation along with two mutations that were not frequently observed ($L_5$ to W and $G_6$ to E).

A summary of the BIAcore app$K_D$ values is given in Table I and indicates a rank order of potency of GH>>418 (SEQ ID NO:12)=417>443 (SEQ ID NO:14)>H5WT (SEQ ID NO:8). This ranking agrees with phage competition data and the BIAcore analysis done at one concentration which showed the rank: H5 wt (SEQ ID NO:8)>445 (SEQ ID NO:13)=432=436. Two peptides, #447 (SEQ ID NO:11) and #418 (SEQ ID NO:12), showed the highest affinity for rGHBP. Both were selected for development of a high throughput screen (HTS) bioassay. Peptide #417: DYKDLCQRLEATWPGWLVGWCA (SEQ ID NO:82); peptide #432: DYKDLCQSLGVTWPGWLAGWCA (SEQ ID NO:83); and peptide #436: DYKDLCQSLGVGWPGWLAGWCA (SEQ ID NO:84).

TABLE I

BIAcore Affinity Measurements of bPeptide binding to rGHBP

| bPeptide | (appK$_D$ [μM]) aPPK$_D$ 1 | aPPK$_D$ 2 |
|---|---|---|
| H5 (SEQ ID NO: 8) | 1.3 | 3.5 |
| #443 (SEQ ID NO: 14) | 0.60 | >10 |
| #447 (SEQ ID NO: 11) | 0.16 | 2.9 |
| #418 (SEQ ID NO: 12) | 0.15 | 0.67 |

Figures 5, 7:
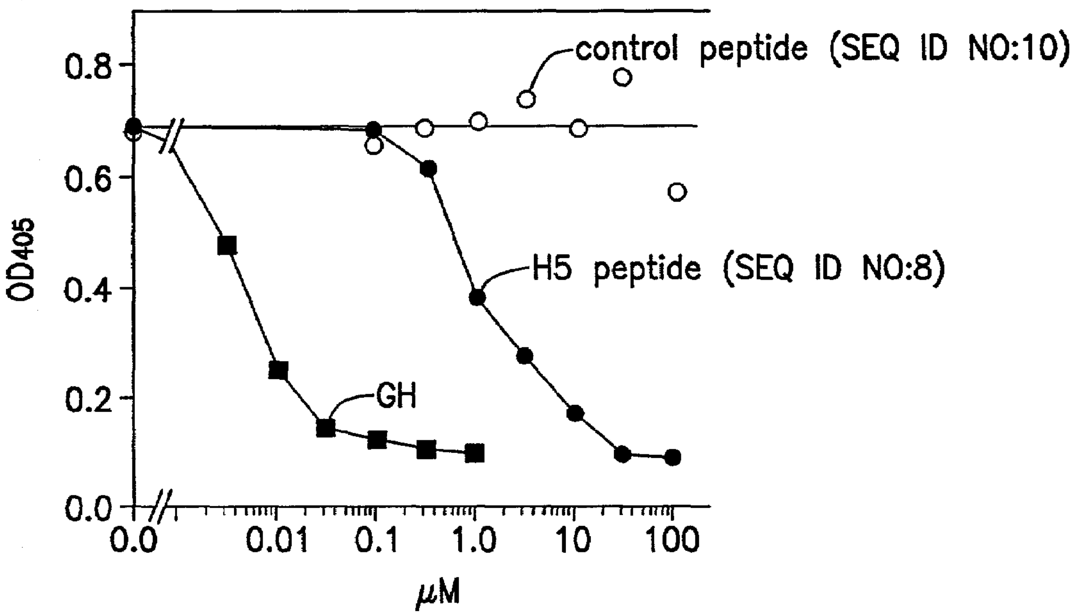
FIG. 5 shows ELISA competition of H5 phage binding to rGHBP by GH, H5 peptide (SEQ ID NO:8), or control peptide (SEQ ID NO:10). Wells were coated with rGHBP (100 ng/well) and blocked as described. Competitor was present prior (1 hr) and during H5 (SEQ ID NO:8) phage incubation (1 hr). Phage was detected with HRP-anti M13 phage antibody and reported at $OD_{405}$ as described. Control peptide (SEQ ID NO:10) contains same amino acids as H5 (SEQ ID NO:8) in randomized order.
FIG. 7 shows the consensus sequence for active site rGHBP binders. H5 sequence (SEQ ID NO: 16) is shown in top line. Amino acids found at various positions are identified along with number of times of such appearances among all positive binders. Consensus sequence (SEQ ID NO:63) shows the most frequent amino acid found at each position in active site binders. Amino acids found ≧3 times are indicated below. Positions in bold were conserved among all binders.
Figure 9A:
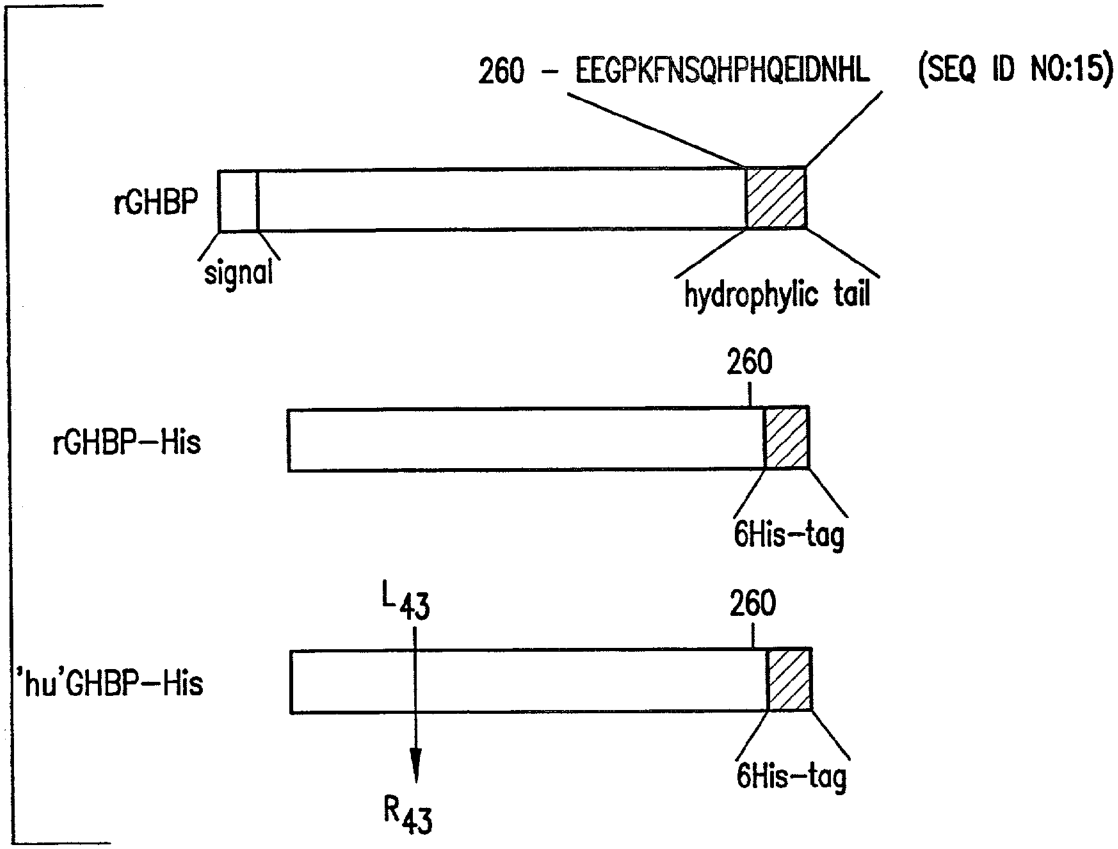
FIG. 9A is a schematic of recombinant expression vectors for rat (r) and 'humanized' ('hu') GHBP constructs; tails as shown, 'hu'=humanized by R43 to L43 amino acid change.
Figure 9B:
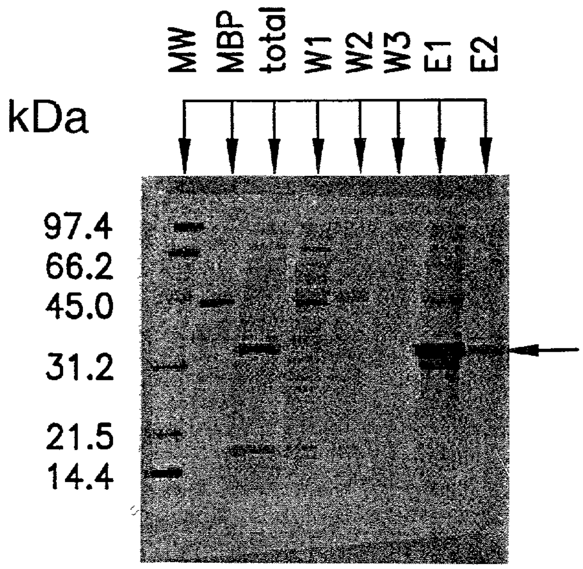
FIG. 9B shows SDS-PAGE analysis of purified rGHBP. MW=molecule weight standards, MBP=maltose binding protein (200 μg); total=total cell extracted, W1–3=soluble fractions after sonication of inclusion bodies, E1-2=8 M urea extractions of inclusion bodies. Kilodaltons are shown in the molecular weight (kDa) scale on left. Position of rGHBP (33 kDa) is shown by the arrow.
Figure 10A:
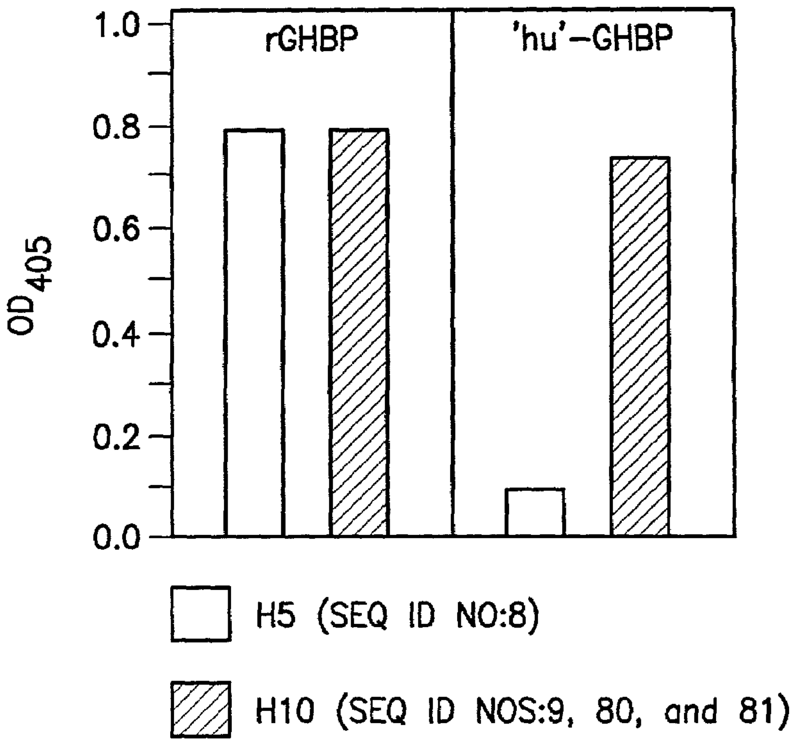
FIG. 10A shows species specificity of H5 (SEQ ID NO:8) binding demonstrated by results from ELISA analysis. Wells were coated with either recombinant rGHBP or 'hu' GHBP (100 ng/well). Additions of H5 (SEQ ID NO:8) and H10 (SEQ ID NOS:9, 80, and 81) phage ($10^{10}$/well) and detection were made as described.
Figure 10B:
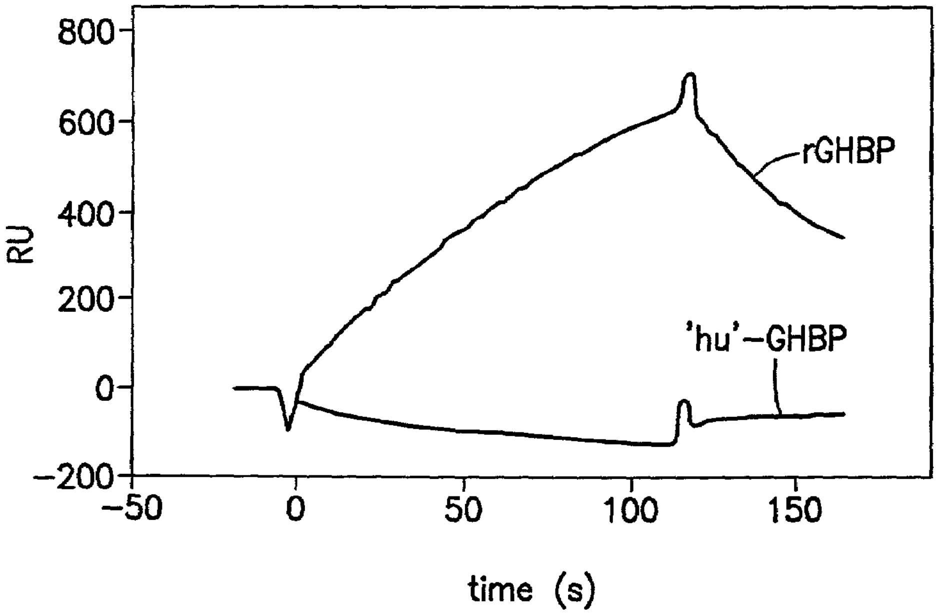
FIG. 10B shows species specificity of H5 (SEQ ID NO:8) binding demonstrated by results from BIAcore analysis. Streptavidin chips were coated with H5 (SEQ ID NO:8) to 1100 RU as described and rGHBP or 'hu' GHBP (500 μg/ml) injected as 30 μl samples.

Growth hormone receptors from different species bind human GH as well as their own GH, however human GHR only binds human or monkey GH. Mutational analysis has demonstrated that R43 accounts for the species specificity of the human GH receptor (Souza, et al., *PNAS*, vol. 82, p. 959–963, 1995). The sequence of rGHBP was altered by PCR to create a "humanized" version ('hu' GHBP; FIG. 9A). Partially purified 'hu'GHBP (FIG. 9B) was tested for binding using ELISA and BIAcore analysis. The results indicated that 'hu' GHBP bound to human GH but not to bovine GH. The $H_{10}$ peptide (SEQ ID NOS:9, 80, and 81; FIG. 5) bound to rGHBP and 'hu' GHBP. Similar to rat GH, the H5WT peptide (SEQ ID NO:8) bound to rGHBP, but not 'hu'GHBP (FIG. 10A). This was confirmed by BIAcore analysis (FIG. 10B).

Example 7

Assays with Synthetic Peptides

Peptide Synthesis

Synthetic peptides were obtained from a commercial supplier (Anaspec). The peptides were supplied greater than 90% pure by HPLC. The molecular weights of the peptides as determined by mass spectroscopy agreed with the expected values.

Equilibrium Binding Constant ($K_D$) Determination

GHBP was immobilized onto one flow-cell of a CM-5 sensor chip (Biosensor) using amine coupling chemistry and the manufacturer's recommended protocol. An unrelated IgG was immobilized in the same manner to another flow cell of the same chip as a control surface. Increasing concentrations of synthetic peptide were injected over both surfaces, and the binding responses were allowed to come to equilibrium. After subtraction of background binding from the control surface, the results were used to derive an equilibrium dissociation constant using Scatchard analysis.

Rank-order Determination of Synthetic Peptides

The rat GHBP (100 μg/ml) was immobilized onto a CM-5 sensor chip using amino coupling chemistry and the manufacturer's recommended protocol. The final surface density was 4000 RU. A monoclonal antibody was immobilized onto another flow cell as a control surface. Peptides (50 μg/ml) were injected at a flow rate of 5 μl/min. Background binding to the control surface was subtracted prior to further analysis.

Competition of H5 Related Peptide Binding to GHBP

The competition of specific bP#447 (SEQ ID NO:11) and bP#418 (SEQ ID NO: 12) binding to the rGHBP was studied in detail using GH (FIG. 12). In these studies, as with those following bGH binding (see FIG. 12A), the competing agents were preincubated with rGHBP before bP addition. The $IC_{50}$ values (FIG. 12B, C, and Table II) showed that GH competed extremely well with either bP#447 (SEQ ID NO:11) or bP#418 (SEQ ID NO: 12) for binding to rGHBP with $IC_{50}$ values of 0.4 and 2 nM, respectively. Maximal competition of total binding by GH was the same for any ligand. From a comparison of $IC_{50}$, GH appeared more potent as inhibitors of bP binding than bGH binding. No competition of either peptide was observed with addition of an antibody preparation specific for another protein.

TABLE II

Summary of TRFD Measurements of Specific Ligand binding to GHBP

| | (nM) ED$_{50}$ | IC$_{50}$ (nM) vs. bGH | vs. bP#447 (SEQ ID NO: 11) | vs. bP#418 (SEQ ID NO: 12) |
|---|---|---|---|---|
| bGH | 20 (n = 1) | — | — | — |
| GH | — | 5 (n = 2) | 0.4 (n = 2) | 2 (n = 1) |
| bP#447 (SEQ ID NO: 11) | 600 (n = 6) | — | — | — |
| bP#418 (SEQ ID NO: 12) | 800 (n = 1) | — | — | — |
| DMSO | | >>3% | >>3% | >>3% |

Wells were coated with rGHBP(100 ng/well) overnight as described. $ED_{50}$ and $IC_{50}$ were calculated from analysis of specific bLigand binding to rGHBP. Competitors were added 1 hr prior to addition of bLigand as described.

Specificity of GHBPs

The biotinylated control peptide (SEQ ID NO:10) was immobilized onto one flow cell of a SA-5 (streptavidin coated) sensor chip to a final density of 700 RU. On a second flow cell, either hGH (1100 RU final density), H5WT peptide (SEQ ID NO:8; 1100 RU final density), or bGH (730 RU final density) was immobilized. GHBP (either rat or humanized) was injected at a concentration of 500 μg/ml with a flow rate of 5 μl/min. Background binding to the control surface was subtracted prior to further analysis.

Example 8

Detection Of the Binding Of Biotinylated GH To GHBP

Figure 11A:
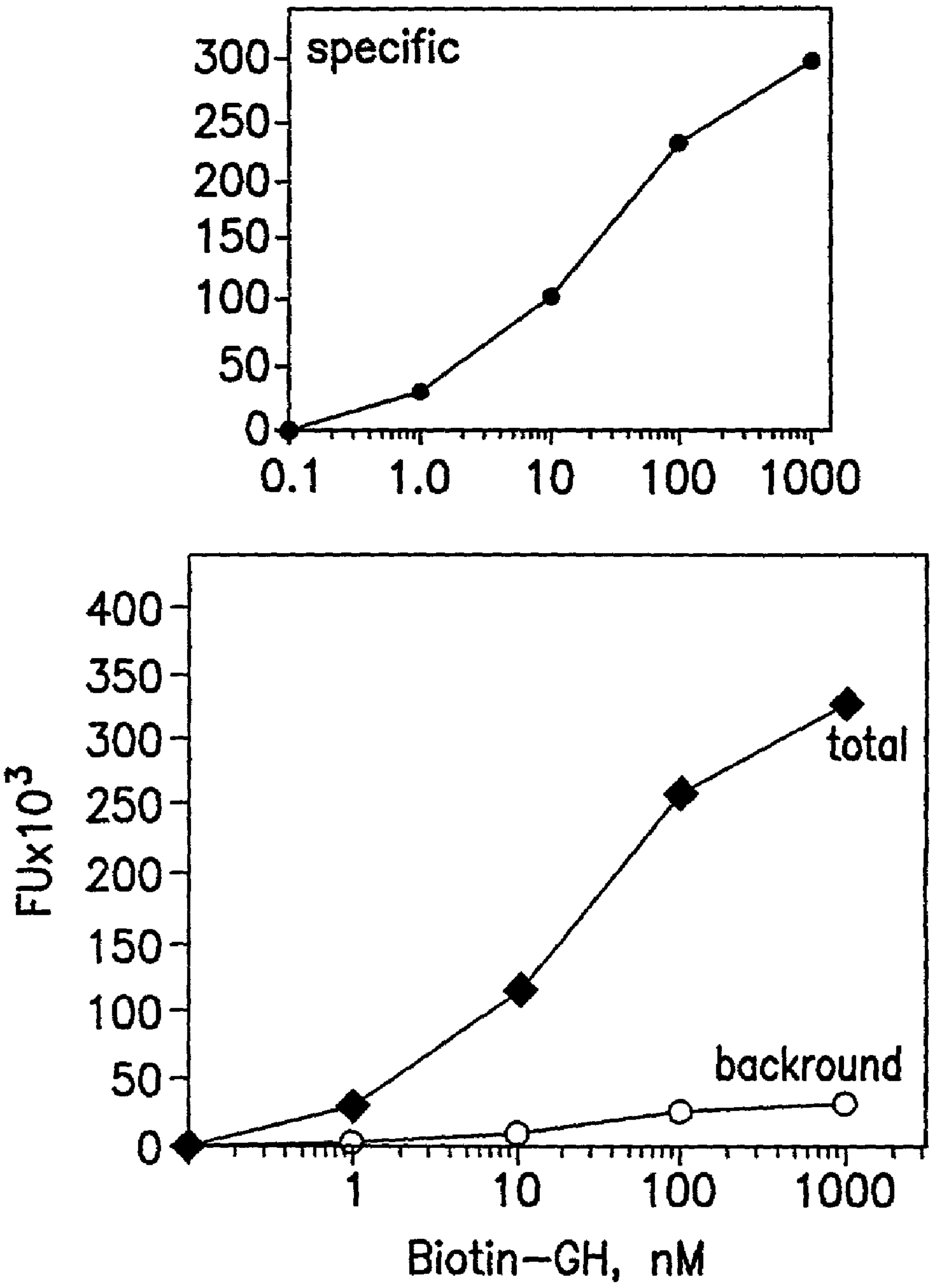
FIGS. 11A–C show binding of bLigands to rGHBP. Wells were coated with rGHBP (100 ng/well) overnight. Increasing concentrations of bLigand were added. Binding was done for 2 hr without (total) or with (background) 1 hr pretreatment with >100 fold excess GH. Insert shows specific binding to rGHBP (i.e., total-background).
Figure 11B:
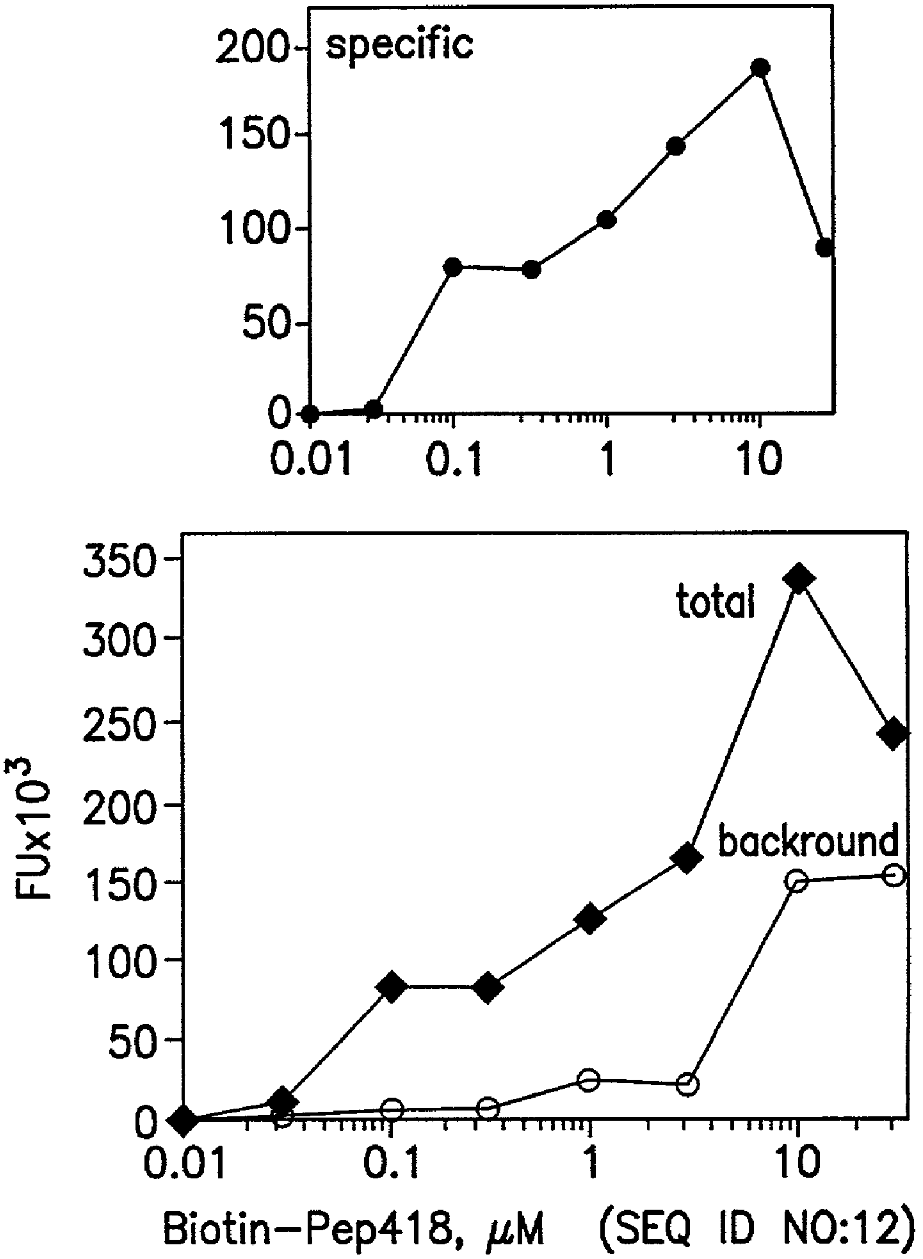
Figure 11C:
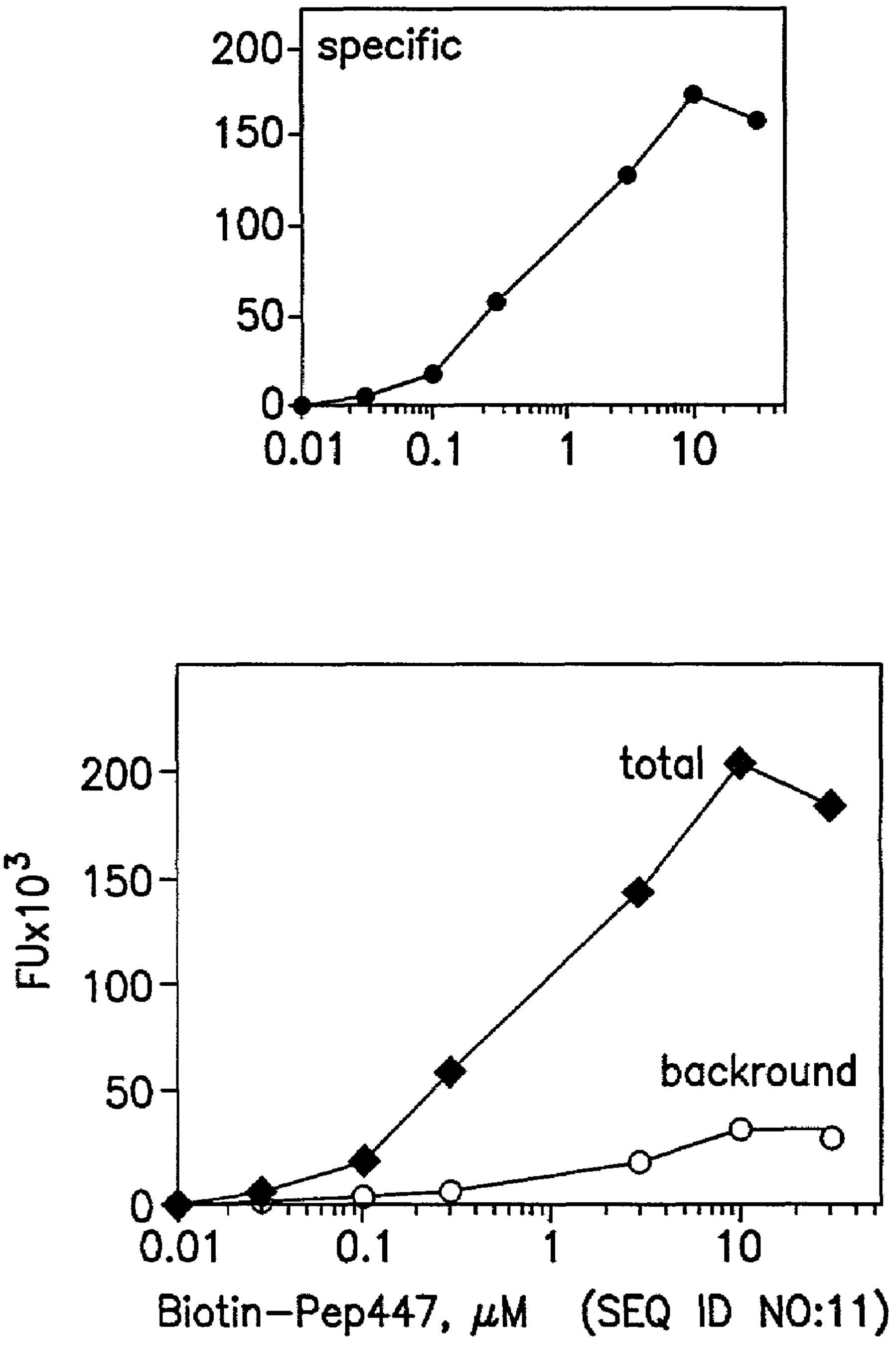
Figure 12A:
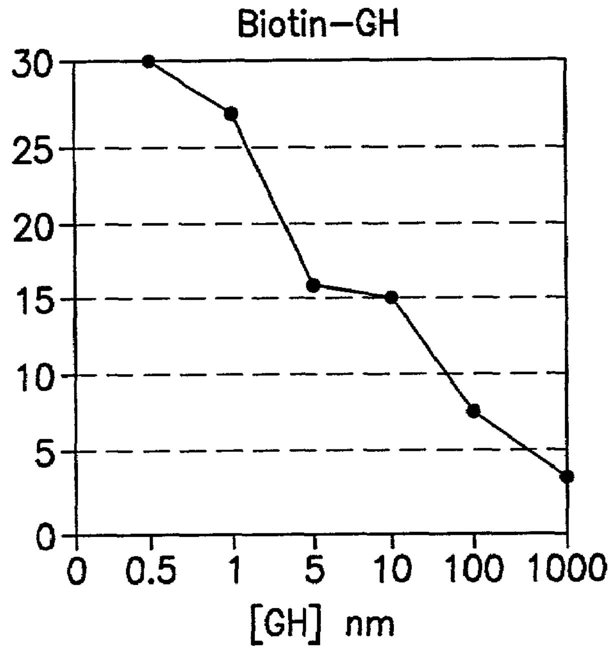
FIGS. 12A–F show competition of bLigand binding by other Agents. Wells were coated with rGHBP (100 ng) overnight. Binding to receptor after 2 hr incubation with bLigand in the presence of competing agent added 1 hr prior to bLigand addition is shown.
Figure 12B:
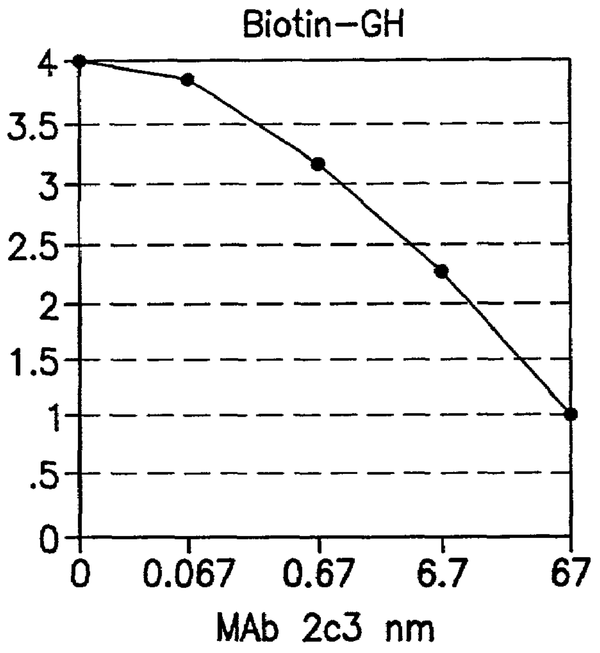
Figure 12C:
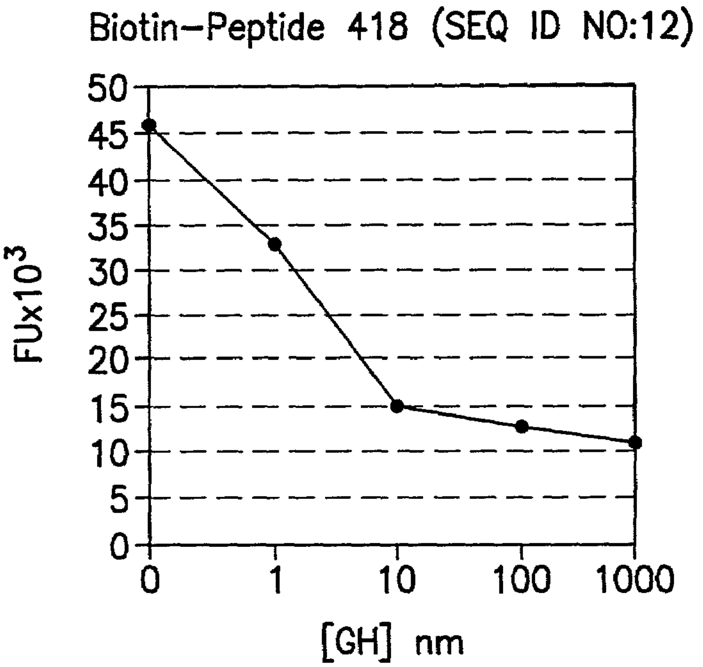
Figure 12D:
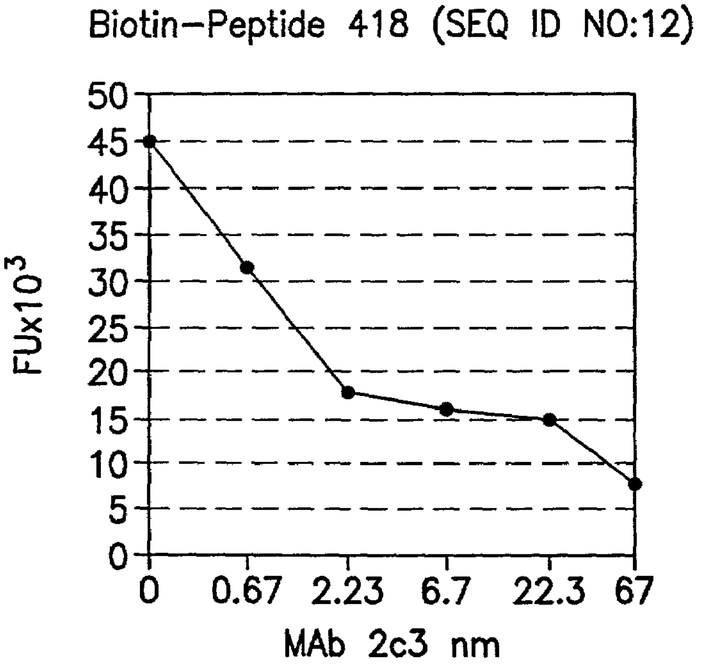
Figure 12E:
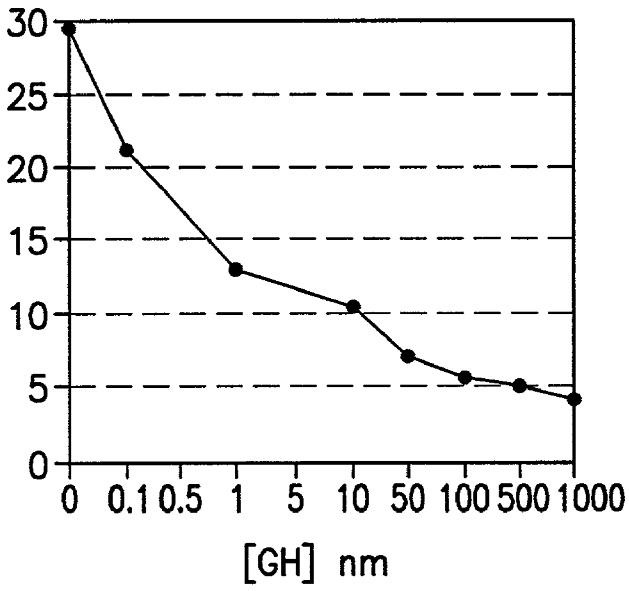
Figure 12F:
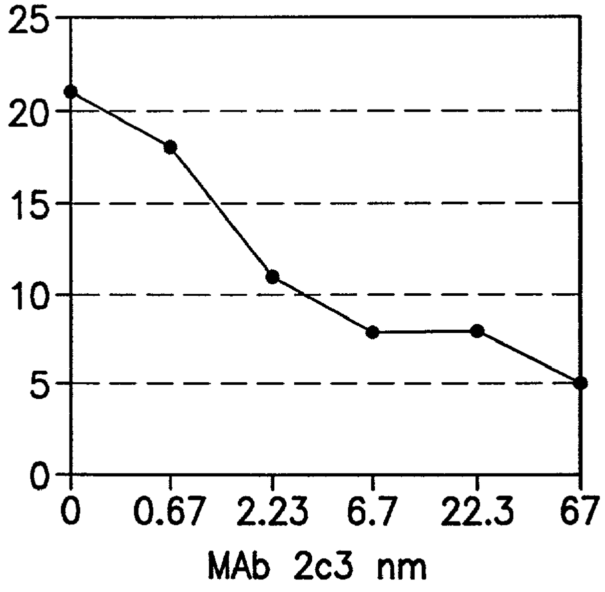

Dose response curves were conducted for bGH (from 0.01 to 1 μM) with wells coated with standard amounts of rGHBP (100 ng/well; FIG. 11). Specific binding to the active site of rGHBP, defined as the difference between binding in the absence and presence of excess GH showed increases from 0.01 to 100 nM but appeared to saturate at 1 μM (FIG. 11A). Half-maximum specific binding ($ED_{50}$) appeared to be ~20 nM (Table II). The specific binding of a fixed concentration of bGH (2 nM) was inhibited by preincubation with non-biotinylated GH or the MAb 2C3 with half-maximal inhibition values ($IC_{50}$) of 5–6 nM (FIG. 11A, B and Table II). The maximum inhibition was approximately equal, as expected with agents competitive for the same active site. Specific binding of bGH was also dependent upon input rGHBP. With 100 ng/well rGHBP coating (standard conditions), the ratio of specific to nonspecific binding (i.e., background binding) was close to 100/1 for bGH over the range 0.5 to 10 nM. Specific binding was detected at concentrations as low as 0.1 nM.

Example 9

Specific Binding of H5-Related Peptides to rGHBP

Specific binding of bP#447 (SEQ ID NO: 11) and bP#418 (SEQ ID NO: 12) to rGHBP standard coated wells was likewise apparent. When tested from 0.001 to 30 μM background binding of bP#447 (SEQ ID NO:11) and bP#418 (SEQ ID NO: 12) was greater than that of bGH at corresponding concentrations (compare FIG. 11A with B and C). Nevertheless, with both bP#447 (SEQ ID NO:11) and bP#418 (SEQ ID NO:12) there was also specific binding which appeared to be saturable and showed respective $ED_{50}$s of 0.7–0.8 μM, respectively (Table II). Specific binding was evident with as little as 0.01–0.3 nM of these two bPs and the best signal to noise (i.e., background binding) ratio for both occurred at 0.3 μM with values of 20/1 to 40/1.

Previous analyses by ELISA and BIAcore indicated that the rank order of potency for binding to the rGHBP (Table I) was bP#447 (SEQ ID NO: 11)=bP#418 (SEQ ID NO:12) >>H5WT (SEQ ID NO:8)≧bP#445 (SEQ ID NO:13). Binding analyses using the Time-Resolved Fluorescence Assay (TRFD) methodology showed that all bP tested were competed by excess GH or MAb2C3 and exhibit the same potency order (see FIG. 13). Even though receptors could not be saturated with H5WT (SEQ ID NO:8) or bP#445 (SEQ ID NO:13), the binding of the two best binders, bP#447 and bP#418 (SEQ ID NO:12), were 10 times better than H5WT (SEQ ID NO:8) or bP#445 (SEQ ID NO: 13).

Figure 13:
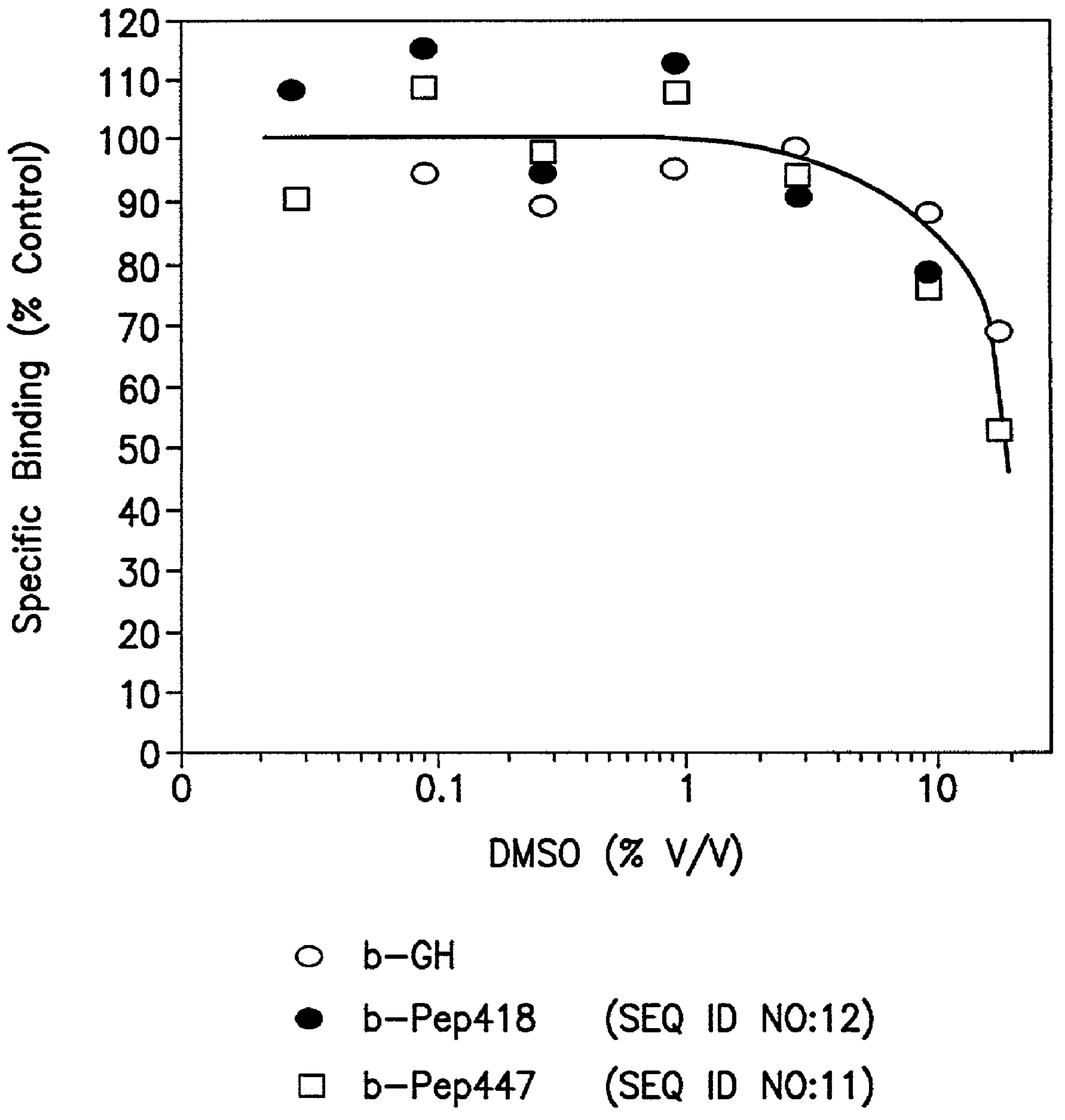
FIG. 13 shows the effect of DMSO on bLigand Binding to rGHBP. Wells were coated with rGHBP (100 ng/well) overnight. Total, background (plus 100 fold excess GH) and specific binding of 2 nM bGH, 0.3 μM bP#418 (SEQ ID NO:12), and 0.3 μM bP#447 (SEQ ID NO: 11) was studied at increasing concentrations of DMSO. Data are given as percent control specific binding seen in absence of DMSO.

In preparation for using this TRFD assay to examine chemical files for compounds that bind to the active site of the GHR, the sensitivity of the assay to DMSO was investigated. This reagent was routinely used as a solvent for synthetic chemicals making up a chemical library, and often reached concentrations of 1% (v/v) in final HTS assays. DMSO was therefore added prior to ligand addition, and total, background and specific binding of bGH (3 nM), bP#447 (SEQ ID NO:11; 0.3 μM) and bP#418 (SEQ ID NO:12; 0.3 μM) were assayed in the presence of 0 to 20% (v/v) DMSO (FIG. 13). No statistically significant inhibition of any of these parameters up to 3% was found. At 10 and 20% DMSO there was a reduction in total, but not background binding indicating a loss in specific binding. DMSO $IC_{50}$ values appeared to be >15% (v/v). These data indicated that either bP could be used at 0.3 μM on the presence of <3% DMSO.

Example 10

Time-Resolved Fluorescence Assay rGHBP (50–200 μg/ml in 50 mM $NaHCO_3$) was coated onto low-fluorescence MaxiSorp (Nunc) plates (100 μl/well) overnight at 4° C. The plates were blocked with PBS containing 2% non-fat milk and 0.05% BSA for 2 hr at room temperature, followed by three PBS washes. For competitions, serial dilutions of unlabelled growth hormone (0.1 nM-100 nM) or MAb 2C3 (0.67–67 nM) were added to the plates (100 μl/well) and incubated at room temperature for 1–2 hr. Biotinylated peptide or biotinylated GH (10× concentrations) were incubated in blocking buffer for 30 min to decrease non-specific binding. Ten microliters of the 10× concentrated material was added to the plates and incubated at room temperature for 1 hr to overnight.

The plates were then washed five times with Tris-buffered saline (pH 7.5) containing 0.1% Tween-20 (TTBS). To each well, 100 μl of europium-labeled streptavidin in DELFIA assay buffer (100 mM Tris-HCl, pH 7.8; 150 mM NaCl; 0.5% BSA; 0.05% bovine Ig; 0.05% NaN3; 0.01% Tween-20) was added and incubated for 1.5 hr at room temperature. The plates were then washed five times with TTBS and tapped dry. Subsequently, 100 μl of DELFIA enhancement solution (100 mM acetone-potassium hydrogen phthalate, pH 3.2; 15 mM 2-naphtyltrifluoroacetate; 50 mM tri(n-octyl)-phosphine oxide; 0.1% Triton X-100) was added to each well, and the plates were shaken for 10 min at room temperature. Fluorescence of each sample well was measured at 615 nm using a DELFIA 1234 fluorometer (EG&G Wallac). General procedure and references as described by Wallac are available in “Lanthanide labeling for time-resolved fluorometry”: Wallac publication 1244–1126-03.

Two milligrams of human or bovine growth hormone were reacted with sulfo-NHS-LC-biotin (Pierce) following the manufacturer’s instructions, and was desalted using a KwikSep column (MW cutoff 5,000; Pierce). The extent of biotin incorporation was determined using 2-(4'-hydroxyazobenzene) benzoic acid (HABA; Pierce) following the manufacturer’s instructions.

Dose response of TRFD of Eu was studied in microtiter wells. Detection was linear over the range 0.2 to 200 fmol with a limit of detection (twice background) of 0.05 fmol. There were 6010 fluorescent units (FU) per fmol of Eu. Binding and detection of Eu(sa), (4.7 mol Eu/mol streptavidin) to wells coated with biotinylated BSA (bBSA) (6 mol biotin/mol BSA) was linear over the entire range tested. The specific fluorescent activity of streptavidin (sa):Eu (with 4 mol Eu/mol sa) was 28 KFU/fmol and the limits of detection (i.e., twice background) were at 0.030 fmol. Coating with bGH was linear up to inputs of 200 ng/well and thereafter appeared to saturate at about 660 ng bGH per well. This was the expected amount based on the manufacture’s information about protein saturation densities of these wells (Nunc manual). These studies showed a limit of detection of bGH (i.e., twice background) of 0.05 fmol bGH. It was next determined whether or not, and within what limits, this assay format detected specifically-bound bGH (or bPeptides) to rGHBP coated wells.

The above results supported the use of this assay procedure as a high throughput screen (HTS) for agents, with affinities for sites on the rat GHBP that bound GH. The studies showed bP#447 (SEQ ID NO: 11) and bP#418 (SEQ ID NO:12) bound in a dose-dependent, saturable manner, and were blocked from binding by agents known to bind to the active site of the receptor. This competition was reproducible and easily quantified. Furthermore, the TRFD assay, which was automatable, was much more sensitive than ELISA. Finally, the assay was not influenced by DMSO if it was kept to <3% (v/v), the concentration of solvent most likely to be encountered in a HTS assay of large chemical libraries.

Example 11

Agonistic and Antagonistic Activity of Peptides

Figure 14A:
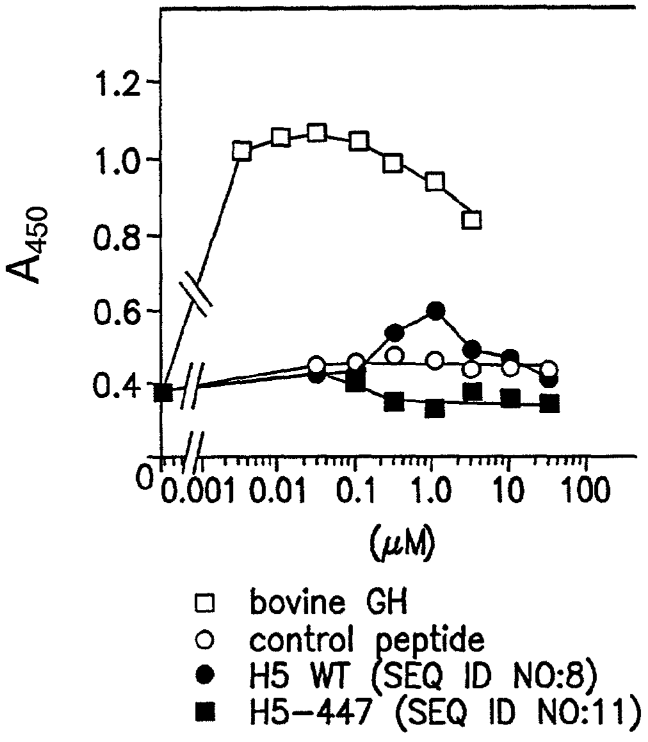
FIG. 14A shows agonistic activities of H5 (SEQ ID NO:8) and 447 (SEQ ID NO:11) tested by cell proliferation assays. Cells transfected with rat GHR (50,000 cells per well) were incubated with either bovine GH, H5 peptide (SEQ ID NO:8), 447 peptide (SEQ ID NO:11) or control peptide (SEQ ID NO:10) for 18 h at 37° C. Experiments were done in triplicate. Background signal $A_{450}$=0.15.
Figure 14B:
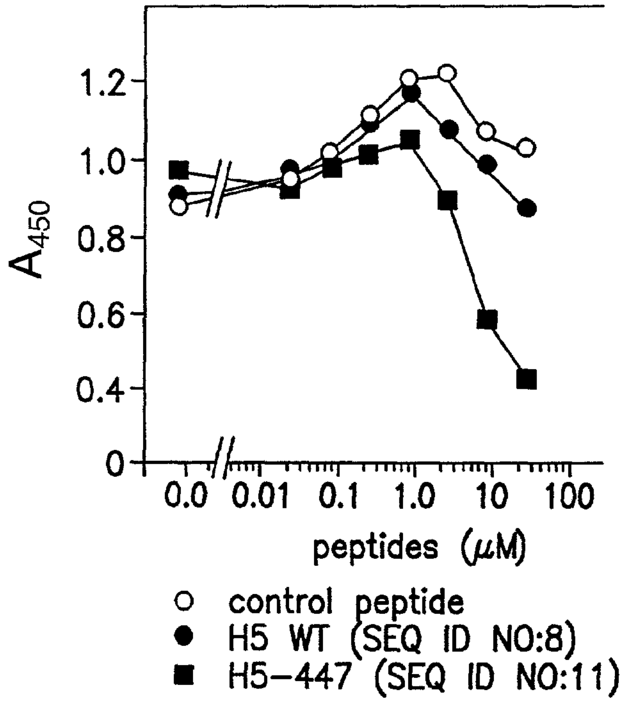
FIG. 14B shows antagonistic activities of H5 and 447 (SEQ ID NOS:8 and 11) tested by cell proliferation assays. Cells transfected with rat GHR (50,000 cells per well) containing 0.003 mM bovine GH were incubated with either control peptide (SEQ ID NO:10), H5 peptide (SEQ ID NO:8) or 447 peptide (SEQ ID NO:11) for 18 h at 37° C. Proliferation was measured using WST-1 reagent. The "*" symbol corresponds to the $A_{450}$ measurement for the cells incubated without GH.

Agonistic and antagonistic activities of the two peptides, H5WT (SEQ ID NO:8) and bP#447 (SEQ ID NO: 1), were tested in FDC-1 cells stably transfected with the gene encoding the rat growth hormone receptor. The resulting cell line required either IL-3 or GH for growth. The cells were grown in RPMI 1640 medium containing 10% FCS (fetal calf serum) and 20 units of IL-3 per ml. Antagonistic activity assays were performed in a total volume of 100 μl in 96 well plates (flat bottom). Cells were seeded at 50,000 cells/well in 50 μl RPMI 1640 (without IL-3) medium containing horse serum instead of FCS to reduce background. To duplicate wells, 50 μl of either growth hormone or peptides at different concentrations was added, followed by incubation for 18 h in a $CO_2$ incubator. Assays to measure the antagonistic activity were performed in a total volume of 100 μl in 96 well plates. Either H5WT peptide (SEQ ID NO:8), bP#447 peptide (SEQ ID NO:11), or control peptide (SEQ ID NO:10) was added to cells containing 0.003 μM of bovine GH and incubated at 37° C. for 18 h in a $CO_2$ incubator. Proliferation assays were performed using WST-1 reagent. The WST-1 tetrazolium salt (light red color) is cleaved to formazan (dark red color) by the succinate-tetrazolium reductase system, which is active only in viable cells. Accordingly, an increase in the number of cells resulted in an increase in the overall activity of the dehydrogenase, which resulted in a higher absorbance at 450 nm. Ten microliters of WST-1 reagent was added and the plates incubated for 1–4 h 37° C. Proliferation was measured by absorbance at 450 nm. The bP#447 peptide (SEQ ID NO: 11) showed an antagonistic activity with an $IC_{50}$ of approximately 5 μM (FIG. 14). Control peptide (SEQ ID NO:10) or H5WT peptide (SEQ ID NO:8) showed no antagonistic activity at the concentrations tested. H5WT peptide (SEQ ID NO:8) showed partial agonistic activity, as indicated by a peak corresponding to 1 μM peptide concentration.

Example 12

Peptide that Binds to Humanized GHBP

A phage displayed peptide that bound to the human GH (hGH) binding site on the humanized form of rat GHBP was produced. Humanized GHBP ('hu' GHBP) contained the single amino acid change of rat GHBP amino acids L43 to R43, and was capable of binding human GH, as shown in FIG. 9. Direct immobilization of 'hu' GHBP was done as described earlier for panning of the secondary H5 library against rat GHBP and used inputs of 'hu' GHBP, prepared as described earlier of 100 μl per well of 10 μg/μl protein. Panning was performed with or without H10 peptide (SEQ ID NO:9; 30 μM) for 4 rounds, and 96 clones were picked.

Clones were tested for the presence of E-tag and binding to 'hu' GHBP, rGHBP, or BSA-coated wells. Those having specific GHBP binding (i.e., at least 2 fold greater binding to the GHBP than BSA) and with an E-tag positive signal were subjected to DNA sequencing. Three different clones were isolated and tested a second time against GHBP plus and minus GH (1 μM) or BSA (1 μM) coated wells as described. In these tests, huGH was used as competitor with 'hu' GHBP coated wells and bovineGH was used as a competitor with rat GHBP coated wells. Clones 13 (SEQ ID NO:2) and HH (SEQ ID NO:3) from the initial library screen were found to bind to both forms of GHBP, however, only clone 13 was blocked by GH. The following open reading frame insertion including the DYKD (SEQ ID NO:79) amino terminal tag and up to the C-terminal E-tag was obtained for these clones; and is shown in Table III:

TABLE III

Clonal Analysis

| Without H10 (SEQ ID NO: 9) | #analyzed | rGHBP | 'hu'GHBP | DNA sequence |
|---|---|---|---|---|
| Round 3 | 95 | 17 | 17 | yes (1 × clone 13) |
| Round 4 | 95 | 17 | 17 | no |
| Round 3 | 95 | 0 | 0 | — |
| Round 4 | 95 | 7 | 7 | yes (1 × clone HH) |

| clones | GHBP | 'hu'GHBP | E-tag | BSA | #copies |
|---|---|---|---|---|---|
| H10 (SEQ ID NO: 9) | + | + | + | − | 22 |
| 13 (SEQ ID NO: 2) | + | + | + | − | 1 |
| HH (SEQ ID NO: 3) | + | + | + | − | 1 |

Sequences clone 13 (SEQ ID NO: 2) DYKDAQWWTTIGSNMFVLPGLRGCTFLPPMQCDREIRVFLVVVH clone HH (SEQ ID NO: 3) DYKDALLHRSRCVRWGKWVCCLPPVGVGGAQANQGMSVQRFRHC Q = TAG suppressor codon ELISA Competition

| | rGHBP | | | 'hu'GHBP | | |
|---|---|---|---|---|---|---|
| | none | +BSA | +bGH | none | +BSA | +hGH |
| H10 (SEQ ID NO: 9) | 0.52 | 0.52 | 0.48 | 0.30 | 0.29 | 0.28 |
| HH (SEQ ID NO: 3) | 0.55 | 0.53 | 0.52 | 0.37 | 0.37 | 0.35 |
| 445 (SEQ ID NO: 13) | 0.45 | 0.44 | 0.16 | 0.14 | 0.11 | 0.12 |
| H5* (SEQ ID NO: 8) | 1.91 | 1.87 | 0.32 | nd | nd | nd |

TABLE III-continued

| | | | | | | |
|---|---|---|---|---|---|---|
| 13* (SEQ ID NO: 2) | 2.01 | 1.98 | 0.29 | nd | nd | nd |
| none | 0.11 | 0.10 | 0.12 | | | |

*= phage concentrated 15×
nd = not determined

The binding of the clone 13 peptide (SEQ ID NO:2) was clearly different from the binding of bovine or rat GH. That is, the clone 13 peptide bound to both human and rat forms of GHBP, whereas rat and bovine GH failed to bind to 'hu' GHBP.

As various changes can be made in the above compositions and methods without departing from the scope and spirit of the invention, it is intended that all subject matter contained in the above description, shown in the accompanying drawings, or defined in the appended claims be interpreted as illustrative, and not in a limiting sense.

The contents of all patents, patent applications, published articles, books, reference manuals, texts and abstracts cited herein are hereby incorporated by reference in their entirety to more fully describe the state of the art to which this invention pertains.

REFERENCES

Baumbach W R, Homer D L, and Logan J S (1989). Genes and Development 3, 1199–1205.

Chen Y C J., Delbrook K, Dealwis C, Mimms L. Mushawar I K, and Mandecki W (1996). *Proc. Natl. Acad. Sci. USA* 93, 1997–2001.

Cwirla S E, Balasubramanian P. Duffin D J, Wagstrom C R, Gates C M, Singer S C, Davis A M, Tansik R L, Mattheakis L C, Boytos C M, Schatz P J, Baccanari D P, Wrighton N C, Barrett R W, and Dower W J (1997). *Science* 276, 1696–99.

Grihalde N D, Chen Y C, Golden A, Gubbins E, and Mandecki W (1995). *Gene* 166, 187–195.

Hopp T P, Prickett K S, Price V, Libby R T, March C J, Cerretti P, Urdal D L, and Conlon P J (1988). *Biotechnology* 6, 1205–1210.

Houghten R A (1985). *Proc. Natl. Acad. Sci. USA* 82, 5131–5135.

Kay B K, Adey N B, He Y S Manfredi J P, Mataragnon A H, and Fowlkes D. M (1993) *Gene* 128, 59–65.

Livnah O, Stura E A, Johnson D L, Middleton S A, Mulcahy L S, Wrighton N C, Dower W J, Jolliffe L K, and Wilson I A (1997). *Science* 273, 469–71.

Mandecki W, Brissette R. Carcamo J, Cheng W, Dedova O, Hsiao K C, Moghe A, Ravera M, Shen H, Tang P, and Blume A (1997). *Display Technologies-Novel Targets and Strategies*. P. Guttry (ed). International Business Communications, Inc., Southborough, Mass., pp. 231–254.

Renschler M F, Bhatt R R, Dower W J, and Levy R (1994). Proc. Natl. Acad. Sci. USA 91, 3623–3627.

Scott J K and Smith G P (1990). *Science* 249, 386–390.

Shukar, S B, Hajduk P J, Meadows R P, and Fesik S W (1996). *Science* 274, 1531–1534.

Souza S C., Frick G P, Wang X, Kopchick J J, Loborb R B, and Goodman H M (1995). *Proc. Natl. Acad. Sci. USA,* 82, 959–963.

Tompkins S M, Rota Pa., Moore J C, and Jensen P E (1993). *J. Immunological Methods* 163, 209–216.

Wang B S, Lumanglas A A, Bona C A, and Moran T M (1996). *Mol Cellular Endocrinology* 116, 223–226.

Wrighton N C, Farrell F X, Chang R, Kashyap A K, Barbone F P, Mulcahy L S, Johnson D L, Barrett R W, Jolliffe L K, and Dower W J (1996). *Science* 273, 458–63.

Yanofsky S. Dak., Balldwin D N, Butler J H, Holden F R, Jacobs J W, Balsubramanian P, Cinn J P, Cwirla S E, Petter-Bhatt E, Whitehom EA, Tate E H, Akeson A, Bowlin T L, Dower W J, and Barrett R W (1996). *Proc. Natl. Acad. Sci. USA* 93, 7381–86.

What is claimed is:

1. An amino acid sequence which binds to growth hormone receptor and comprises the sequence LCQRLGVGWPGWLSGWCA (SEQ ID NO:76), wherein the growth hormone receptor is selected from the group consisting of bovine and human growth hormone receptor.

2. A pharmaceutical composition comprising an amino acid sequence which binds to growth hormone receptor and comprises the sequence LCQRLGVGWPGWLSGWCA (SEQ ID NO:76), and a physiologically acceptable carrier, excipient, or diluent.

3. A kit for identifying a compound that binds to growth hormone receptor comprising growth hormone binding protein and an amino acid sequence which binds to growth hormone receptor and comprises the sequence LCQRLGVGWPGWLSGWCA (SEQ ID NO:76).

4. The kit according to claim 3, wherein the growth hormone binding protein and the amino acid sequence comprise a complex.

5. The kit according to claim 3, wherein the growth hormone binding protein is labeled with a label selected from the group consisting of radioisotopes, fluorescent molecules, chemiluminescent molecules, enzymes, and biotin.

6. The kit according to claim 3, wherein the amino acid sequence is labeled with a label selected from the group consisting of radioisotopes, fluorescent molecules, chemiluminescent molecules, enzymes, and biotin.

* * * * *

SEQUENCE LISTING

<160> NUMBER OF SEQ ID NOS: 84

<210> SEQ ID NO 1
<211> LENGTH: 79
<212> TYPE: DNA
<213> ORGANISM: Artificial Sequence
<220> FEATURE:
<223> OTHER INFORMATION: H5 oligonucleotide

<400> SEQUENCE: 1
ctacaaagac ctgtgtcaga gtttgggggt tacgtatccg ggttggttgg cggggtggtg 60
tgcggcggcc gcagtgtga 79

<210> SEQ ID NO 2
<211> LENGTH: 44
<212> TYPE: PRT
<213> ORGANISM: Artificial Sequence
<220> FEATURE:
<223> OTHER INFORMATION: clone 13 peptide -continued

<400> SEQUENCE: 2

Asp Tyr Lys Asp Ala Gln Trp Trp Thr Thr Ile Gly Ser Asn Met Phe
1 5 10 15

Val Leu Pro Gly Leu Arg Gly Cys Thr Phe Leu Pro Pro Met Gln Cys
20 25 30

Asp Arg Glu Ile Arg Val Phe Leu Val Val Val His
35 40

<210> SEQ ID NO 3
<211> LENGTH: 44
<212> TYPE: PRT
<213> ORGANISM: Artificial Sequence
<220> FEATURE:
<223> OTHER INFORMATION: clone hh peptide

<400> SEQUENCE: 3

Asp Tyr Lys Asp Ala Leu Leu His Arg Ser Arg Cys Val Arg Trp Gly
1 5 10 15

Lys Trp Val Cys Cys Leu Pro Pro Val Gly Val Gly Gly Ala Gln Ala
20 25 30

Asn Gln Gly Met Ser Val Gln Arg Phe Arg His Cys
35 40

<210> SEQ ID NO 4
<211> LENGTH: 16
<212> TYPE: PRT
<213> ORGANISM: Artificial Sequence
<220> FEATURE:
<223> OTHER INFORMATION: consensus sequence, wherein X1 is S, R, T, N, H, or A; X2 is L, W, or F; X3 is G, A, V, P, Q, E, or R; X4 is V, I, A, L, D, E, P, or F; X5 is T, G, S, R, K, N, A, L, or W; X6 is Y, W, F, or Q;
<220> FEATURE:
<223> OTHER INFORMATION: X7 is L, V, or I; X8 is A, T, S, V, W, or D; X9 is G, A, S, or R

<400> SEQUENCE: 4

Cys Gln Xaa Xaa Xaa Xaa Xaa Xaa Pro Gly Trp Xaa Xaa Xaa Trp Cys
1 5 10 15

<210> SEQ ID NO 5
<211> LENGTH: 20
<212> TYPE: PRT
<213> ORGANISM: Artificial Sequence
<220> FEATURE:
<223> OTHER INFORMATION: #445 peptide derivative

<400> SEQUENCE: 5

Leu Cys Gln Arg Leu Gly Val Gly Trp Pro Gly Trp Leu Ser Gly Trp
1 5 10 15

Cys Ala Lys Lys
20

<210> SEQ ID NO 6
<211> LENGTH: 20
<212> TYPE: PRT
<213> ORGANISM: Artificial Sequence
<220> FEATURE:
<223> OTHER INFORMATION: #418 peptide derivative

<400> SEQUENCE: 6

Leu Cys Gln Ser Trp Gln Val Thr Trp Pro Gly Trp Leu Ala Gly Trp
1 5 10 15

-continued

```
Cys Ala Lys Lys
            20


<210> SEQ ID NO 7
<211> LENGTH: 40
<212> TYPE: PRT
<213> ORGANISM: Artificial Sequence
<220> FEATURE:
<223> OTHER INFORMATION: clone 13 peptide derivative

<400> SEQUENCE: 7

Ala Gln Trp Trp Thr Thr Ile Gly Ser Asn Met Phe Val Leu Pro Gly
  1               5                  10                  15

Leu Arg Gly Cys Thr Phe Leu Pro Pro Met Gln Cys Asp Arg Glu Ile
            20                  25                  30

Arg Val Phe Leu Val Val Val His
        35                  40


<210> SEQ ID NO 8
<211> LENGTH: 22
<212> TYPE: PRT
<213> ORGANISM: Artificial Sequence
<220> FEATURE:
<223> OTHER INFORMATION: H5 peptide

<400> SEQUENCE: 8

Asp Tyr Lys Asp Leu Cys Gln Ser Leu Gly Val Thr Tyr Pro Gly Trp
  1               5                  10                  15

Leu Ala Gly Trp Cys Ala
            20


<210> SEQ ID NO 9
<211> LENGTH: 14
<212> TYPE: PRT
<213> ORGANISM: Artificial Sequence
<220> FEATURE:
<223> OTHER INFORMATION: H10 peptide

<400> SEQUENCE: 9

Trp Leu Gly Cys Tyr Phe Val Ala Gly Val Val Ala Cys Val
  1               5                  10


<210> SEQ ID NO 10
<211> LENGTH: 22
<212> TYPE: PRT
<213> ORGANISM: Artificial Sequence
<220> FEATURE:
<223> OTHER INFORMATION: control peptide

<400> SEQUENCE: 10

Asp Tyr Lys Asp Trp Cys Leu Thr Leu Gln Pro Leu Val Trp Ala Ser
  1               5                  10                  15

Gly Gly Gly Tyr Cys Ala
            20


<210> SEQ ID NO 11
<211> LENGTH: 22
<212> TYPE: PRT
<213> ORGANISM: Artificial Sequence
<220> FEATURE:
<223> OTHER INFORMATION: #447 peptide

<400> SEQUENCE: 11

Asp Tyr Lys Asp Leu Cys Gln Arg Leu Gly Val Gly Trp Pro Gly Trp
  1               5                  10                  15
```

-continued

```
Leu Ser Gly Trp Cys Ala
            20


<210> SEQ ID NO 12
<211> LENGTH: 22
<212> TYPE: PRT
<213> ORGANISM: Artificial Sequence
<220> FEATURE:
<223> OTHER INFORMATION: #418 peptide

<400> SEQUENCE: 12

Asp Tyr Lys Asp Leu Cys Gln Ser Trp Gln Val Thr Trp Pro Gly Trp
  1               5                  10                  15

Leu Ala Gly Trp Cys Ala
            20


<210> SEQ ID NO 13
<211> LENGTH: 22
<212> TYPE: PRT
<213> ORGANISM: Artificial Sequence
<220> FEATURE:
<223> OTHER INFORMATION: #445 peptide

<400> SEQUENCE: 13

Asp Tyr Lys Asp Leu Cys Gln Arg Leu Gly Val Gly Trp Pro Gly Trp
  1               5                  10                  15

Leu Ala Gly Trp Cys Ala
            20


<210> SEQ ID NO 14
<211> LENGTH: 22
<212> TYPE: PRT
<213> ORGANISM: Artificial Sequence
<220> FEATURE:
<223> OTHER INFORMATION: #443 peptide

<400> SEQUENCE: 14

Asp Tyr Lys Asp Leu Cys Gln Arg Leu Gly Val Thr Trp Pro Gly Trp
  1               5                  10                  15

Leu Ala Gly Trp Cys Ala
            20


<210> SEQ ID NO 15
<211> LENGTH: 19
<212> TYPE: PRT
<213> ORGANISM: Artificial Sequence
<220> FEATURE:
<223> OTHER INFORMATION: hydrophilic tail of rGHBP construct

<400> SEQUENCE: 15

Glu Glu Gly Pro Lys Phe Asn Ser Gln His Pro His Gln Glu Ile Asp
  1               5                  10                  15

Asn His Leu


<210> SEQ ID NO 16
<211> LENGTH: 18
<212> TYPE: PRT
<213> ORGANISM: Artificial Sequence
<220> FEATURE:
<223> OTHER INFORMATION: H5 peptide secondary library starting sequence

<400> SEQUENCE: 16

Leu Cys Gln Ser Leu Gly Val Thr Tyr Pro Gly Trp Leu Ala Gly Trp
  1               5                  10                  15
```

-continued

Cys Ala

<210> SEQ ID NO 17
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 17

Leu Cys Gln Ser Leu Gly Ile Thr Tyr Pro Gly Trp Leu Ala Gly Trp
1 5 10 15

Cys Ala

<210> SEQ ID NO 18
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 18

Leu Cys Gln Thr Leu Gly Val Thr Tyr Pro Gly Trp Leu Ala Gly Trp
1 5 10 15

Cys Ala

<210> SEQ ID NO 19
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 19

Leu Cys Gln Ser Leu Gly Val Lys Tyr Pro Gly Trp Leu Ala Gly Trp
1 5 10 15

Cys Ala

<210> SEQ ID NO 20
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 20

Leu Cys Gln Ser Leu Gly Val Lys Tyr Pro Gly Trp Leu Thr Gly Trp
1 5 10 15

Cys Ala

<210> SEQ ID NO 21
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 21

Leu Cys Gln Ser Leu Gly Val Thr Tyr Pro Gly Trp Leu Ser Gly Trp
1 5 10 15

Cys Ala

-continued

<210> SEQ ID NO 22
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 22

Leu Cys Gln Ser Leu Gly Val Ala Tyr Pro Gly Trp Leu Ala Gly Trp
1               5                   10                  15

Cys Ala

<210> SEQ ID NO 23
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 23

Leu Cys Gln Ser Leu Gly Val Thr Phe Pro Gly Trp Leu Ser Gly Trp
1               5                   10                  15

Cys Ala

<210> SEQ ID NO 24
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 24

Leu Cys Gln Ala Leu Gly Val Thr Tyr Pro Gly Trp Leu Ala Gly Trp
1               5                   10                  15

Cys Ala

<210> SEQ ID NO 25
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 25

Leu Cys Gln Ser Leu Gly Val Ser Tyr Pro Gly Trp Leu Ala Gly Trp
1               5                   10                  15

Cys Ala

<210> SEQ ID NO 26
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 26

Leu Cys Gln Ser Leu Gly Val Thr Tyr Pro Gly Trp Leu Ala Ala Trp
1               5                   10                  15

Cys Arg

<210> SEQ ID NO 27
<211> LENGTH: 18
<212> TYPE: PRT
<213> ORGANISM: Artificial Sequence -continued
<220> FEATURE:
<223> OTHER INFORMATION: H5 peptide secondary library sequence

<400> SEQUENCE: 27

Leu Cys Gln Ser Leu Gly Val Thr Tyr Pro Gly Trp Leu Asp Gly Trp
1 5 10 15

Cys Ala

<210> SEQ ID NO 28
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 28

Leu Cys Gln Ser Leu Gly Val Ser Tyr Pro Gly Trp Leu Val Gly Trp
1 5 10 15

Cys Ala

<210> SEQ ID NO 29
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 29

Leu Cys Gln Thr Leu Gly Val Lys Tyr Pro Gly Trp Leu Ala Gly Trp
1 5 10 15

Cys Ala

<210> SEQ ID NO 30
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 30

Leu Cys Gln Ser Leu Gly Leu Thr Tyr Pro Gly Trp Leu Ala Gly Trp
1 5 10 15

Cys Gly

<210> SEQ ID NO 31
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 31

Leu Cys Gln Ser Leu Gly Glu Ala Tyr Pro Gly Trp Leu Ala Gly Trp
1 5 10 15

Cys Ala

<210> SEQ ID NO 32
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 32

-continued

```
Leu Cys Gln Arg Leu Gly Leu Thr Trp Pro Gly Trp Leu Ala Gly Trp
  1               5                  10                  15

Cys Ala


<210> SEQ ID NO 33
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 33

Leu Cys Gln Ser Leu Gly Val Trp Trp Pro Gly Trp Leu Ala Gly Trp
  1               5                  10                  15

Cys Ala


<210> SEQ ID NO 34
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 34

Leu Cys Gln Ser Leu Gly Phe Thr Tyr Pro Gly Trp Leu Ala Gly Trp
  1               5                  10                  15

Cys Ala


<210> SEQ ID NO 35
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 35

Leu Cys Gln Ser Leu Gly Val Thr Tyr Pro Gly Trp Leu Ala Gly Trp
  1               5                  10                  15

Cys Ser


<210> SEQ ID NO 36
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 36

Leu Cys Gln Ser Leu Gly Val Thr Tyr Pro Gly Trp Leu Val Gly Trp
  1               5                  10                  15

Cys Ala


<210> SEQ ID NO 37
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 37

Leu Cys Gln Ser Leu Ala Val Thr Tyr Pro Gly Trp Leu Ala Gly Trp
  1               5                  10                  15
```

-continued

Cys Ala

<210> SEQ ID NO 38
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 38

Leu Cys Gln Ser Leu Gly Val Arg Tyr Pro Gly Trp Leu Ala Gly Trp
1 5 10 15

Cys Ala

<210> SEQ ID NO 39
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 39

Leu Cys Gln Ser Leu Gly Val Leu Tyr Pro Gly Trp Leu Ala Gly Trp
1 5 10 15

Cys Ala

<210> SEQ ID NO 40
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 40

Leu Cys Gln Ser Leu Gly Pro Thr Tyr Pro Gly Trp Leu Ala Gly Trp
1 5 10 15

Cys Ala

<210> SEQ ID NO 41
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 41

Met Cys Gln Ser Leu Gly Val Thr Tyr Pro Gly Trp Leu Ala Gly Trp
1 5 10 15

Cys Ala

<210> SEQ ID NO 42
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 42

Leu Cys Gln Ser Leu Gly Leu Arg Tyr Pro Gly Trp Leu Ala Gly Trp
1 5 10 15

Cys Ala

<210> SEQ ID NO 43

-continued

<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 43

Leu Cys Gln Ser Leu Gly Val Thr Tyr Pro Gly Trp Leu Ala Gly Trp
1 5 10 15

Cys Gly

<210> SEQ ID NO 44
<211> LENGTH: 18
<212> TYPE: PRT
<213> ORGANISM: Artificial Sequence
<220> FEATURE:
<223> OTHER INFORMATION: H5 peptide secondary library sequence #443

<400> SEQUENCE: 44

Leu Cys Gln Arg Leu Gly Val Thr Trp Pro Gly Trp Leu Ala Gly Trp
1 5 10 15

Cys Ala

<210> SEQ ID NO 45
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 45

Leu Cys Gln Ser Leu Gly Ala Thr Trp Pro Gly Trp Leu Ala Gly Trp
1 5 10 15

Cys Ala

<210> SEQ ID NO 46
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 46

Leu Cys Gln Arg Leu Gly Val Ser Trp Pro Gly Trp Leu Ala Gly Trp
1 5 10 15

Cys Ala

<210> SEQ ID NO 47
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 47

Leu Cys Gln Ser Leu Pro Val Arg Tyr Pro Gly Trp Leu Ser Gly Trp
1 5 10 15

Cys Ser

<210> SEQ ID NO 48
<211> LENGTH: 18
<212> TYPE: PRT
<213> ORGANISM: Artificial Sequence
<220> FEATURE:

-continued

```
<223> OTHER INFORMATION: H5 peptide secondary library sequence H5-445

<400> SEQUENCE: 48

Leu Cys Gln Arg Leu Gly Val Gly Trp Pro Gly Trp Leu Ala Gly Trp
  1               5                  10                  15

Cys Ala


<210> SEQ ID NO 49
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 49

Leu Cys Gln Asn Leu Gly Ile Thr Trp Pro Gly Trp Leu Ala Gly Trp
  1               5                  10                  15

Cys Ala


<210> SEQ ID NO 50
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 50

Leu Cys Gln Ser Leu Gly Val Thr Phe Pro Gly Trp Leu Ala Gly Trp
  1               5                  10                  15

Cys Ala


<210> SEQ ID NO 51
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 51

Leu Cys Gln Ser Leu Gly Asp Lys Tyr Pro Gly Trp Leu Ala Gly Trp
  1               5                  10                  15

Cys Ala


<210> SEQ ID NO 52
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 52

Leu Cys Gln Ser Leu Gly Val Gly Trp Pro Gly Trp Leu Ala Gly Trp
  1               5                  10                  15

Cys Ala


<210> SEQ ID NO 53
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 53
```

-continued

Leu Cys Gln Arg Leu Gly Val Thr Trp Pro Gly Trp Leu Thr Gly Trp
1 5 10 15

Cys Ala

<210> SEQ ID NO 54
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 54

Leu Cys Gln Ser Leu Gly Val Thr Tyr Pro Gly Trp Leu Thr Gly Trp
1 5 10 15

Cys Ala

<210> SEQ ID NO 55
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 55

Leu Cys Gln Ser Leu Gly Ala Thr Tyr Pro Gly Trp Leu Trp Gly Trp
1 5 10 15

Cys Ala

<210> SEQ ID NO 56
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 56

Leu Cys Gln Ser Leu Gly Asp Thr Tyr Pro Gly Trp Leu Ala Gly Trp
1 5 10 15

Cys Ala

<210> SEQ ID NO 57
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 57

Leu Cys Gln Ser Leu Gly Val Gly Tyr Pro Gly Trp Leu Ala Gly Trp
1 5 10 15

Cys Ala

<210> SEQ ID NO 58
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 58

Leu Cys Gln Ser Leu Gly Val Thr Trp Pro Gly Trp Leu Ala Gly Trp
1 5 10 15

Cys Ala

-continued

<210> SEQ ID NO 59
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 59

Leu Cys Gln Arg Leu Gly Val Thr Tyr Pro Gly Trp Leu Ala Gly Trp
1 5 10 15

Cys Ala

<210> SEQ ID NO 60
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 60

Leu Cys Gln Arg Leu Gly Ala Thr Trp Pro Gly Trp Leu Ala Gly Trp
1 5 10 15

Cys Ala

<210> SEQ ID NO 61
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 61

Leu Cys Gln Ser Leu Gly Val Asn Trp Pro Gly Trp Leu Ala Gly Trp
1 5 10 15

Cys Ala

<210> SEQ ID NO 62
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 62

Leu Cys Gln Ser Leu Gly Val Ser Trp Pro Gly Trp Leu Thr Gly Trp
1 5 10 15

Cys Ala

<210> SEQ ID NO 63
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 63

Leu Cys Gln Arg Leu Gly Ile Gly Trp Pro Gly Trp Leu Ala Gly Trp
1 5 10 15

Cys Ala

<210> SEQ ID NO 64
<211> LENGTH: 18

-continued

<212> TYPE: PRT
<213> ORGANISM: Artificial Sequence
<220> FEATURE:
<223> OTHER INFORMATION: H5 peptide secondary library sequence

<400> SEQUENCE: 64

Leu Cys Gln Arg Leu Gly Val Gly Trp Pro Gly Trp Val Ala Gly Trp
1 5 10 15

Cys Ala

<210> SEQ ID NO 65
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 65

Leu Cys Gln Ser Leu Gly Val Ser Tyr Pro Gly Trp Leu Thr Gly Trp
1 5 10 15

Cys Ala

<210> SEQ ID NO 66
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 66

Leu Cys Gln His Leu Gly Val Thr Trp Pro Gly Trp Leu Ala Gly Trp
1 5 10 15

Cys Ala

<210> SEQ ID NO 67
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 67

Leu Cys Gln Ser Leu Gly Ile Gly Tyr Pro Gly Trp Leu Thr Gly Trp
1 5 10 15

Cys Ala

<210> SEQ ID NO 68
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 68

Leu Cys Gln Arg Leu Val Val Gly Trp Pro Gly Trp Leu Ala Gly Trp
1 5 10 15

Cys Ala

<210> SEQ ID NO 69
<211> LENGTH: 18
<212> TYPE: PRT
<213> ORGANISM: Artificial Sequence
<220> FEATURE:
<223> OTHER INFORMATION: H5 peptide secondary library sequence -continued

<400> SEQUENCE: 69

Leu Cys Gln Arg Leu Gly Val Thr Trp Pro Gly Trp Ile Ala Gly Trp
1 5 10 15

Cys Ala

<210> SEQ ID NO 70
<211> LENGTH: 18
<212> TYPE: PRT
<213> ORGANISM: Artificial Sequence
<220> FEATURE:
<223> OTHER INFORMATION: H5 peptide secondary library sequence #418

<400> SEQUENCE: 70

Leu Cys Gln Ser Trp Gln Val Thr Trp Pro Gly Trp Leu Ala Gly Trp
1 5 10 15

Cys Ala

<210> SEQ ID NO 71
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 71

Leu Cys Gln Arg Leu Glu Ala Thr Trp Pro Gly Trp Leu Val Gly Trp
1 5 10 15

Cys Ala

<210> SEQ ID NO 72
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 72

Leu Cys Gln Ser Leu Gly Val Gly Trp Pro Gly Trp Leu Thr Gly Trp
1 5 10 15

Cys Ala

<210> SEQ ID NO 73
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 73

Leu Cys Gln Ser Leu Gly Val Asn Tyr Pro Gly Trp Leu Ala Gly Trp
1 5 10 15

Cys Ala

<210> SEQ ID NO 74
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 74

Leu Cys Gln Arg Phe Gly Val Gly Phe Pro Gly Trp Leu Ala Gly Trp

-continued 1 5 10 15

Cys Ala

<210> SEQ ID NO 75
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 75

Leu Cys Gln Asn Leu Gly Val Thr Trp Pro Gly Trp Leu Ala Gly Trp
1 5 10 15

Cys Ala

<210> SEQ ID NO 76
<211> LENGTH: 18
<212> TYPE: PRT
<213> ORGANISM: Artificial Sequence
<220> FEATURE:
<223> OTHER INFORMATION: H5 peptide secondary library sequence #447

<400> SEQUENCE: 76

Leu Cys Gln Arg Leu Gly Val Gly Trp Pro Gly Trp Leu Ser Gly Trp
1 5 10 15

Cys Ala

<210> SEQ ID NO 77
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 77

Leu Cys Gln Arg Leu Gly Val Thr Trp Pro Gly Trp Leu Trp Gly Trp
1 5 10 15

Cys Ala

<210> SEQ ID NO 78
<211> LENGTH: 18
<212> TYPE: PRT
<213> ORGANISM: Artificial Sequence
<220> FEATURE:
<223> OTHER INFORMATION: H5 peptide secondary library sequence

<400> SEQUENCE: 78

Leu Cys Gln Ser Leu Arg Val Arg Gln Pro Gly Trp Leu Ser Gly Trp
1 5 10 15

Cys Ala

<210> SEQ ID NO 79
<211> LENGTH: 4
<212> TYPE: PRT
<213> ORGANISM: Artificial Sequence
<220> FEATURE:
<223> OTHER INFORMATION: Flag-tag sequence

<400> SEQUENCE: 79

Asp Tyr Lys Asp
1

<210> SEQ ID NO 80

-continued

<211> LENGTH: 6
<212> TYPE: PRT
<213> ORGANISM: Artificial Sequence
<220> FEATURE:
<223> OTHER INFORMATION: H10 peptide

<400> SEQUENCE: 80

Asp Tyr Lys Asp Phe Pro
1 5

<210> SEQ ID NO 81
<211> LENGTH: 20
<212> TYPE: PRT
<213> ORGANISM: Artificial Sequence
<220> FEATURE:
<223> OTHER INFORMATION: H10 peptide

<400> SEQUENCE: 81

Val Cys Trp Arg Ala His Phe Arg Ser Leu Gly Leu Glu Ser Ser Phe
1 5 10 15

Ala Gly Gly Gly
20

<210> SEQ ID NO 82
<211> LENGTH: 22
<212> TYPE: PRT
<213> ORGANISM: Artificial Sequence
<220> FEATURE:
<223> OTHER INFORMATION: #417 peptide

<400> SEQUENCE: 81

Asp Tyr Lys Asp Leu Cys Gln Arg Leu Glu Ala Thr Trp Pro Gly Trp
1 5 10 15

Leu Val Gly Trp Cys Ala
20

<210> SEQ ID NO 83
<211> LENGTH: 22
<212> TYPE: PRT
<213> ORGANISM: Artificial Sequence
<220> FEATURE:
<223> OTHER INFORMATION: #432 peptide

<400> SEQUENCE: 81

Asp Tyr Lys Asp Leu Cys Gln Ser Leu Gly Val Thr Trp Pro Gly Trp
1 5 10 15

Leu Ala Gly Trp Cys Ala
20

<210> SEQ ID NO 84
<211> LENGTH: 22
<212> TYPE: PRT
<213> ORGANISM: Artificial Sequence
<220> FEATURE:
<223> OTHER INFORMATION: #436 peptide

<400> SEQUENCE: 81

Asp Tyr Lys Asp Leu Cys Gln Ser Leu Gly Val Gly Trp Pro Gly Trp
1 5 10 15

Leu Ala Gly Trp Cys Ala
20